United States Patent
Cottingham et al.

(10) Patent No.: US 11,198,721 B2
(45) Date of Patent: *Dec. 14, 2021

(54) METHODS FOR TREATMENT OF INFLAMMATORY DISEASE OR IL-6-MEDIATED CONDITION WITH GP130 PROTEIN

(71) Applicant: Ferring B.V., Hoofddorp (NL)

(72) Inventors: Ian Cottingham, St-Prex (CH); Niclas Axel Petri, Copenhagen (DK)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,092

(22) PCT Filed: Dec. 1, 2015

(86) PCT No.: PCT/IB2015/002459
§ 371 (c)(1),
(2) Date: May 31, 2017

(87) PCT Pub. No.: WO2016/087941
PCT Pub. Date: Jun. 9, 2016

(65) Prior Publication Data
US 2017/0320932 A1    Nov. 9, 2017

Related U.S. Application Data

(60) Provisional application No. 62/086,054, filed on Dec. 1, 2014.

(51) Int. Cl.
*A61K 38/00* (2006.01)
*C07K 14/715* (2006.01)
*C07K 14/54* (2006.01)

(52) U.S. Cl.
CPC ...... *C07K 14/7155* (2013.01); *C07K 14/5412* (2013.01); *A61K 38/00* (2013.01); *C07K 2319/30* (2013.01)

(58) Field of Classification Search
CPC ............ C07K 14/5412; C07K 2319/30; C07K 2319/00; A61P 19/02
See application file for complete search history.

(56) References Cited

U.S. PATENT DOCUMENTS

| | | | |
|---|---|---|---|
| 4,751,180 A | 6/1988 | Cousens et al. |
| 5,457,035 A | 10/1995 | Baum et al. |
| 5,783,672 A | 7/1998 | Mosley et al. |
| 6,605,703 B1 | 8/2003 | Schaeffer et al. |
| 6,838,076 B2 | 1/2005 | Patton et al. |
| 6,887,687 B2 | 5/2005 | Anderson |
| 7,534,862 B2 | 5/2009 | Seegert et al. |
| 7,629,147 B2 | 12/2009 | Seegert et al. |
| 7,851,182 B2 | 12/2010 | Seegert et al. |
| 8,895,012 B2 | 11/2014 | Watzig et al. |
| 9,034,817 B2 | 5/2015 | Watzig et al. |
| 9,573,989 B2 | 2/2017 | Watzig et al. |
| 2002/0012962 A1 | 1/2002 | Stahl et al. |
| 2003/0118510 A1 | 6/2003 | Patton et al. |
| 2007/0270334 A1 | 11/2007 | Seegert et al. |
| 2008/0227155 A1 | 9/2008 | Seegert et al. |
| 2010/0028367 A1 | 2/2010 | Watzig et al. |
| 2013/0243744 A1 | 9/2013 | Betenbaugh |
| 2014/0178378 A1 | 6/2014 | Watzig et al. |
| 2015/0361157 A1 | 12/2015 | Watzig et al. |
| 2018/0282396 A1 | 10/2018 | Cottingham et al. |
| 2020/0123226 A1 | 4/2020 | Cottingham et al. |

FOREIGN PATENT DOCUMENTS

| | | |
|---|---|---|
| CN | 103221537 A | 7/2013 |
| DE | 19941897 A1 | 3/2001 |
| EP | 0442724 A2 | 8/1991 |
| EP | 1148065 A1 | 10/2001 |
| EP | 1491554 A1 | 12/2004 |
| EP | 1630232 A1 | 3/2006 |
| EP | 1801121 A1 | 6/2007 |
| JP | 2004/182638 A | 7/2004 |
| WO | WO-94/12520 A1 | 6/1994 |
| WO | WO-95/33059 A2 | 12/1995 |
| WO | WO-00/18932 A2 | 4/2000 |
| WO | WO-01/58957 A2 | 8/2001 |
| WO | WO-03/008454 A2 | 1/2003 |
| WO | WO-2004/113383 A2 | 12/2004 |
| WO | WO-2006/021453 A2 | 3/2006 |
| WO | WO-2007/071449 A1 | 6/2007 |
| WO | WO-2008/000516 A2 | 1/2008 |
| WO | WO-2009/049881 A1 | 4/2009 |
| WO | WO-2016/089206 A2 | 6/2016 |

OTHER PUBLICATIONS

O'Brien et al. Use of azathioprine or 6-mercaptopurine in the treatment of Crohn's disease. Gastroenterology. Jul. 1991;101(1):39-46.*
Al-Gwaiz, L.A. and Babay, H.H., The Diagnostic Value of Absolute Neutrophil Count, Band Count and Morphologic Changes of Neutrophils in Predicting Bacterial Infections, Med. Princ. Pract., 16: 344-347 (2007).
Ancey et al., A fusion protein of the gp130 and interleukin-6Ralpha ligangbinding domains acts as a potent interleukin-6 inhibitor, J. Biol. Chem., 278(19):16968-16972 (2003).
Atreya et al., Blockade of interleukin 6 trans signaling suppresses T-cell resistance against apoptosis in chronic intestinal inflammation: Evidence in Crohn disease and experimental colitis in vivo, Nature Medicine, 6(5):583-588 (2000).
Barkhausen et al., Selective blockade of interleukin-6 trans-signaling improves survival in a murine polymicrobial sepsis model, Crit. Care Med., 39(6):1407-1413 (2011).

(Continued)

*Primary Examiner* — Dong Jiang
(74) *Attorney, Agent, or Firm* — Choate, Hall & Stewart LLP; Rolando Medina; Dana M. Daukss

(57) ABSTRACT

A selective IL-6-trans-signalling inhibitor can be used to treat a variety of IL-6-mediated conditions, including inflammatory diseases and cancer. The inhibitor can safely be administered to humans at a variety of doses. Moreover, the inhibitor lessens deleterious effects associated with other IL-6 inhibitors such as lowering neutrophil counts, platelet counts and levels of C-reactive protein.

17 Claims, 11 Drawing Sheets

Specification includes a Sequence Listing.

(56) References Cited

OTHER PUBLICATIONS

Bayliss et al., A humanized anti-IL-6 antibody (ALD518) in non-small cell lung cancer, Expert Opin. Viol. Ther. Early Online, pp. 1-6 (Oct. 17, 2011).
Becker et al., TGF-ß Suppresses Tumor Progression in Colon Cancer by Inhibition of IL-6 trans-Signaling, Immunity, 21:491-501 (2004).
Bitter et al., Expression and Secretion Vectors for Yeast, Methods in Enzymology, 153:515:545 (1987).
Boulanger et al., Hexameric Structure and Assembly of the Interleukin-6/IL-6 α-Receptor/gp 130 Complex, Science 300:2101-2104 (2003).
Boulanger et al., Hexameric Structure and Assembly of the Interleukin-6/IL-6 α-Receptor/gp 130 Complex, Science 300:2101-2104 (2003). Supplemental Information. Materials & Methods, 5 pages (2003).
Broglie et al., Light-Regulated Expression of a Pea Ribulose-1,5-Bisphosphate Carboxylase Small Subunit Gene in Transformed Plant Cells, Science, 224:838-843 (1984).
Canfield et al., The Binding Affinity of Human IgG for its High Affinity Fc Receptor is Determined by Multiple Amino Acides in the CH2 Domain and Its Modulated by the Hinge Region, J. Exp. Med., 173:1483-1491 (1991).
Chalaris et al., Apoptosis is a natural stimulus of IL6R shedding and contributed to the proinflammatory trans-signaling function of neutrophils, Blood, 110(6):1748-1755 (2007).
Chow et al., A structural template for gp130-cytokine signaling assemblies, Biochimica et Biophasica Acta, 1592(3):225-235 (2002).
Chow et al., In vitro reconstruction of recognition and activation complexes between interleukin-6 and gp130, Biochemistry, 40(25):7593-7603 (2001).
Colbere-Garapin et al., A New Dominant Hybrid Selective Marker for Higher Eukaryotic Cells, J. Mol. Biol., 150:1-14 (1981).
Coruzzi et al., Tissue-specific and light-regulated expression of a pea nuclear gene encoding the small subunit of ribulose-1,5-bisphosphate carboxylase, The EMBO Journal, 3(8):1671-1679 (1984).
Cunningham et al., Receptor and antibody epitopes in human growth hormone identified by homolog-scanning mutagenesis, Science, 10(4896):1330-1336 (1989).
Cunningham et al., High-resolution epitope mapping of hGH-receptor interactions by alanine-scanning mutagenesis, Science 244(4908):1081-1085 (1989).
Darnell, Jr., STATs and Gene Regulation, Science, 277:1630-1635 (1997).
Deisenhofer, Crystallographic Refinement and Atomic Models of a Human Fc Fragment and Its Complex with Fragment B of Protein A from *Staphylococcus aureus* at 2.9- and 2.8-A Resolution, Biochem., 20(9):2361-2370 (1981).
Duncan et al., Localization of the binding site for the human high-affinity Fc receptor on IgG, Nature, 332:563-564 (1988).
EBI Accession No. AAY92205, Fusion polypeptide 616, IL-6 trap (Aug. 1, 2000).
EBI Accession No. AEF92945, Wild-type egp130fc, Seq ID: 11 #2 (May 4, 2006).
Eck et al., Goodman & Gilmans The Pharmacological Basis of Therapeutics, Ninth Edition, McGraw-Hill, pp. 77-101 (1996).
Economides et al., Cytokine traps: multi-component, high-affinity blockers of cytokine action, Nature Medicine, 9(1):47-52 (2003).
Economides et al., Designer Cytokines: Targeting Actions to Cells of Choice, Science, 270:1351-1353 (1995).
Edwards et al., The Formation of a structure with the features of synovial lining by subcutaneous injection of air: an in vivo tissue culture system, J. Pathology, 134:147-156 (1981).
Engelhard et al., The insect tracheal system: A conduit for the systemic spread of Autographa califonica M nuclear polyhedrosis virus, Proc. Natl., Acad. Sci., 91:3224-3227 (1994).
Fingl et al., The Pharmacological Basis of Therapeutics, Goodman Gilman Eds. Macmilliam Publishing Co., pp. 1-46 (1975).
Fischer et al., A bioactive designer cytokine for human hematopoietic progenitor cell expansion, Nature Biotechnology, 15:142-145 (1997).

Friend et al., Phase I Study of an Engineered Aglycosylated Humanized CD3 Antibody in Renal Transplant Rejection, Transplantation, 68(11):1632-1637 (1999).
Fuglsang, Codon optimizer: a freeware tool for codon optimization, Protein Expr. Purif., 2:247-249 (2003).
Gao et al., UpGene: Application of Web-Based DNA Codon Optimization Algorithm, Biotechnol. Prog., 20:443-448 (2004).
Gellissen et al., New yeast expression platforms based on mehtylotrophic Hansenula polymorpha and Pichia pastoris and on dimorphic Arxula adeninivorans and Yarrowia lipolytica—A comparison, FEMS Yeast Research, 5:1079-1096 (2005).
Giese et al., Dimerization of the cytokine receptors gp130 and LIFR analysed in single cells, Journal of Cell Science, 118(21):5129-5140 (2005).
Gomord et al., Biopharmaceutical production in plants: problems, solutions and opportunities, TRENDS in Biotechnology, 23(11):559-561 (2005).
Goodson et al., Site-Directed Pegylation of Recombinant Interleukin-2 At Its Glygosylation Site, Biotechnology, 8:343-346 (1990).
Grace et al., Structural and Biologic Characterization of Pegylated Recombinant IFN-α2b, Jr. of Interferon and Cytokine Research, 21:1103-1115 (2001).
Greenhill et al., Il-6 Trans-Signaling Modulates TLR4-Dependent Inflammatory Responses via STAT3, J. of Immunology, 186:1199-1208 (2011).
Grotzinger et al., IL-6 Type Cytokine Receptor Complexes: Hexamer, Tetramer or Both?, Biol. Chem., 380:803-813 (1999).
Grotzinger et al., The Family of the IL-6-Type Cytokines: Specificity and Promiscuity of the Receptor Complexes, Proteins: Structure, Function and Genetics, 27:96-109 (1997).
Hammer et al., Increased inflammation and lethalityof Dusp1$^{-/-}$ mice in plymicrobial peritonitis models, Immunology, 131:395-404 (2010).
Hartman et al., Two-dominant-acting selectable markers for gene transfer studies in mammalian cells, Proc. Natl. Acad. Sci., 85:8047-8051 (1988).
Herold et al., Anti-CD3 Monoclonal Antibody of New-Onset Type I Diabetes Mellitus, New England J. of Med., 346(22):1692-1698 (2002).
Hobbs et al., Genetic Engineering, McCraw Hill, New York, NY, pp. 191-196 (1992).
Horsten et al., The membrane distal half of gp130 is responsible for the formation of ternary complex with IL-6 and the IL-6 and receptor, FEBS Lett., 360(1):43-46 (1995).
Inoue et al., A highly enhanced thrombopoietic activity by monomethoxy polyethylene glycol-modified recombinant human interleukin-6, J. Lab. Clin. Med., 124(4):529-536 (1994).
International Search Report for PCT/IB2015/002459, 5 pages (dated May 11, 2016).
International Search Report for PCT/NL2015/050837, 7 pages (dated Jun. 2, 2016).
Isaacs et al., Therapy with Monoclonal Antibodies. II The Contribution of Fcγ Receptor Binding and the Influence of CH1 and CH3 Domains on in Vivo Effector Function, J. of Immunology, 161:3862-3869 (1998).
JAVA, Codon Adaptation Tool—JCAT http://www.jcat.de retrieved Oct. 9, 2008.
Jefferis et al., IgG-Fc-mediated effector functions: molecular definition of interaction sites for effector ligands and the role of glycosylation, Immunological Review, 163:59-76 (1998).
Jefferis et al., Interaction sites on human IgG-Fc for FcγR: current models, Immunology Letters, 82:57-65 (2002).
Jefferis et al., Recognition sites on human IgG for Fcγ receptors: the role of flycosylation, Immunology Letters, 44:111-117 (1995).
Jones et al., Loss of CD4 T Cell IL-6R Expression during Inflammation Underlines a Role for IL-6 Trans-Signaling in the Local Maintenance of Th17 Cells, J. Immunol., 184:2130-2139 (2010).
Jostock et al., Immunoadhesins of interleukin-6 and the IL-6/soluble IL-6R fusion protein hyper-IL-6, Jr. of Immunological Methods, 223:171-183 (1999).
Jostock et al., Soluble gp130 is the nature inhibitor of soluble interleukin-6 receptor transsignaling responses, Eur. J. Biochem., 268:160-167 (2001).

(56) References Cited

OTHER PUBLICATIONS

Kallen, K.J., The role of transsignaling via the agonistic soluble IL-6 receptor in human diseases, Biochem. Biophys. Acta, 1592:323-343 (2002).
Katre, Immunogenicity of Recombinant IL-2 Modified by Covalent Attachment of Polyethylene Glycol., Jr. of Immunology, 144(1):209-213 (1990).
Kishimoto et al., Interleukin-6 Family of Cytokines and gp130, Blood, 86(4):1243-1254 (1995).
Kohler et al., Continuous cultures of fused cells secreting antibody of predefined specificity, Nature, 256:495-497 (1975).
Krapp et al., Structural Analysis of Human IgG-Fc Glycoforms Reveals Correlation Between Glycosylation and Structural Integrity, J. Mol. Biol., 325:979-989 (2003).
Krause et al., Rheumatoid arthritis synoviocyte survival is dependent on Stat3, J. Immunol., 169(11):6610-6616 (2002).
Lazar et al., Transforming Growth Factor α: Mutation of Aspartic Acid 47 and Leucine 48 Results in Different Biological Activities, Molecular & Cellular Biol., 8(3):1247-1252 (1988).
Lee et al., Interleukin-6 Induces S100A9 Expression in Colonic Epithelial Cell through STAT3 Activation in Experimental Ulcerative Colitis, PLoS One, 7(9):e38801. doi:10.1371/journal.pone.0038801 (2012).
Levy et al., What does Stat3 do?, J. Clin. Invest., 109(9):1143-1148 (2002).
Lo et al., IL-6 Trans-Signaling in Formation and Progression of Malignant Ascites in Ovarian Cancer, Cancer Res., 71(2):424-434 (2011).
Logan et al., Adenovirus tripartite leader sequence enhances translation of mRNAS later after infection, Proc. Natl. Acad. Sci. USA, 84:3655-3659 (1984).
Lowy et al., Isolation of Transforming DNA: Cloning the Hamster aprt Gene, Cell, 22:817-823 (1980).
Lund et al., Human FcYRI and FcYRII Interact with Distinct But Overlapping Sites on Human IgG1, Journal of Immunology, 147(8):2657-2662 (1991).
Macauley-Patrick et al., Heterologous protein production using the Pichia pastoris expression system, Yeast, 22:249-270 (2005).
Matsumiya et al., Structural Comparison of Fucosylated and Nonfucosylated Fc Fragments of Human Immunoglobulin G1, J. Mol. Biol., 368:767-779 (2007).
Matsumoto et al., Essential Roles of Il-6 Trans-Signaling in Colonic Epithelial Cells, Induced by the IL-6/Soluble-IL-6 Receptor Derived from Lamina Propria Macrophasees on Development of Colitis-Associated Premalignant Cancer in a Murine Model, J. of Immunol., 184: 1543-1551 (2010).
Mees, S.T. et al., Inhibition of Interleukin-6-Transsignaling via gp130-Fc in Hemorrhagic Shock and Sepsis, Journal of Surgical Research, 157(2): 235-242 (2009).
Mikayama et al., Molecular cloning and functional expression of cDNA encoding glycosylation-inhibiting factor, Proc. Natl., Acad. Sci., 90:10056-10060 (1993).
Mitsuyama et al., STAT3 activation via interleukin 6 trans-signaling contributes to ileitis in SAMP1/Yit mice, Gut, 5:1263-1269 (2006).
Mitsuyama, K. et al., Therapeutic Strategies for Targeting the IL-6/STAT3 Cytokine Signaling Pathway in Inflammatory Bowel Disease, Anticancer Research, 27: 3749-3756 (2007).
Murry, L.E., Agrobacterium-Mediated plant transformation in McGraw Hill Yearbook of Science and Technology, McGraw Hill, New York, pp. 191-196 (1992).
Müllberg et al., IL-6 receptor independent stimulation of human gp130 by viral IL-6, J. Immunol., 164(9):4672-4677 (2000).
Nakamura et al., Codon usage tabulated from the international DNA sequence databases, Nucleic Acids Research, 24(1):214-215 (1996).
Nishimoto et al., Anticytokine therapy in autoimmune diseases, Intern. Med., 38(2):178-182 (1999).
Nishimoto, T., A new role of ran GTPase, Biochem. Biophys. Res. Commun., 262(3):571-574 (1999).
Nose et al., Biological significance of carbohydrates chains on monoclonal antibodies, Proc. Natl. Acad. Sci., 80:6632-6636 (1983).
Nowell et al., Therapeutic Targeting of IL-6 Trans-Signaling Counteracts STAT3 Control of Experimental Inflammatory Arthritis, J. of Immunology, 182:614-622 (2009).
Oganesyan et al., Structural characterization of mutated, ADCC-enhances human Fc fragment, Molecular Immunology, 45:1872-1882 (2008).
Oppmann et al., Alternative assay procedures for cytokines and soluble receptors of the IL-6 family, J. of Immunological Methods, 195:153-159 (1996).
Peipp et al., Molecular Engineering III: Fc Engineering, Handbook of Therapeutic Antibodies, pp. 171-196 (2007).
Pepinsky et al., Improved Pharmacokinetic Properties of Polyethylene Glycol-Modified Form of Interferon-ß-1a with Preserved in Vitro Bioactivity, Jr. of Pharmacology and Experimental Therapeutics, 297(3):1059-1066 (2001).
Peters et al., In vivo and in vitro activities of the gp130-Stimulating Designer Cytokine Hyper-IL-6, J. of Immunology, 161:3575-3581 (1998).
Pettit et al., Structure-Function Studies of Interleukin 15 using Site-specific Mutagenesis, Polyethylen Glycol Conjugation, and Homology Modeling, Jr. of Biological Chemistry, 272(4):2312-2318 (1997).
Rabe et al., Transgenic blockade of interleukin 6 transsignaling abrogates inflammation, Blood, 111:1021-1028 (2008).
Rakemann et al., The designer cytokine hyper-interleukin 6 is a potent activator of STAT3-dependent gene transcription in vivo and in vitro, J. Biol. Chem., 274(3):1257-1266 (1999).
Rhodes et al., Identification of MRF4; a new member of the muscle regulatory factor gene family, Genes Dev., 3:2050-2061 (1989).
Rhodes et al., Transformation of Maize by Electroporation of Embryos, Methods in Molecular Biology, 55:121-131 (1995).
Rose-John et al., Studies on the structure and regulation of the human hepatic interleukin-6 receptor, Eur. J. Biochem., 190:79-83 (1990).
Rose-John, S. et al., The IL-6/sIL-6R complex as a novel target for the therapeutic approaches, Expert Opin. Ther. Targets, 11(5): 613-624 (2007).
Sambrook et al., Molecular Cloning: A Laboratory Manual—2nd Edition, Cold Spring Harbor Laboratory Press, pp. I-XXXVIII (1989).
Scharf et al., Heat stress promoters and transcription factors, Results and Problems in Cell Differentiation, 20:125-162 (1994).
Schutt et al., Supplemental Material—Transsignaling of Interleukin-6 Crucially Contributes to Atherosclerosis in Mice, Arterior cler Throm. Biol., 32(2):1-26 (2011).
Schutt et al., Transsignaling of Interleukin-6 Crucially Contributes to Atherosclerosis in Mice, Arterior cler Throm. Vasc. Biol., 32(2):281-290 (2011).
Siam et al., Choosing and using Schzosaccharomyces pombe plasmids, Methods, 33:189-198 (2004).
Sommer, J. et al., Alternative Intronic Polyadenylation Generates the Interleukin-6 Trans-signaling Inhibitor sgp130-E10, Journal of Biological Chemistry, 289(32): 22140-22150 (2014).
Sondermann et al., The 3.2-Å crystal structure of the human IgG1 Fc fragment-FcγRIII complex, Nature, 406:267-273 (2000).
Sprang et al., Cytokine structural taxonomy and mechanisms of receptor engagement, Current Opinion in Structural Biology, 3:815-827 (1993).
Stoger et al., Sowing the seeds of success: pharmaceutical proteins from plants, Current Opinion in Biotechnology, 16:167-173 (2005).
Suzuki et al., CIS3/SOCS3/SSI3 plays a negative regulatory role in STAT3 activation and intestinal inflammation, J. Exp. Med., 193(4):471-481 (2001).
Takamatsu et al., Expression of bacterial chloramphenicol acetyltransferase gene in tobacco plants mediated by TMV-RNA, The EMBO Journal, 6(2):307-311 (1987).
Tanaka et al., Cloning of novel soluble gp130 and detection of its neutralizing autoantibodies in rheumatoid arthritis, J. Clin. Invest., 106:137-144 (2000).
Tang et al., Studies on the PEGylation of Protein at a Specific Site: Sulfhydryl-PEGylation of 97Cys-IFN-gamma, Sheng Wu Hua Xue Yu Sheng Wu Wu Li Xue Bao (Shanghai), 28(3):312-215 (1996) (in Chinese with English abstract).

(56) References Cited

OTHER PUBLICATIONS

Tao et al., Studies of Aglycosylated Chimeric Mouse-Human IgG, J. of Immunology, 143(8):2595-2601 (1989).
Tenhumber et al., Characterization of Mutants of the Soluble CP130 Protein in Terms of their binding affinity against the IL6/SIL6R Complex, Cytokine Abstracts, Abstract 152, 39:42 (2007).
Tenhumberg, S. et al., Structure-guided optimization of the interleukin-6 trans-signaling antagonist sgp130, Journal of Biological Chemistry, 283(40): 27200-27207 (2008).
Tsunoda et al., Selective enhancement of thrombopoetic activity of PEGylated interleukin 6 by a simple procedure using a reversible aminoprotective reagent, BR. J. Haematol., 112:181-188 (2001).
Turkson et al., STAT proteins: novel molecular targets for cancer drug discovery, Oncogene, 19(56):6613-6626 (2000).
UnitProt Interleukin-6 receptor beta chain precursor. HIBI: Interleukin signal transducer, XP002322123 retrieved from EBI Database accession No. P40189 abstract, Feb. 1, 1995 (Feb. 1, 1995).
Utset et al., Modified Anti-CD3 Therapy in Psoriatic Arthritis: A Phase I/II Clinical Trial, J. Rheum., 29:1907-1913 (2002).
Voet et al., Biochemistry, John Wiley and Sons, Inc., pp. 126 and 228-234 (1990).
Vriend et al., What if: A molecular modeling and drug design program, J. Mol. Graphics, 8:52-56 (1990).
Wada et al., Codon usage tabulated from the GenBank genetic sequence data, Nucleic Acids Re., 18(Supplemental):2367-2411 (1990).
Waetzig et al., p38 Mitogen-Activated Protein Kinase Is Activated and Linked to TNF-α Signaling in Inflammatory Bowel Disease, Jr. of Immunology, 168:5342-5351 (2002).
Waetzig, G.H. et al., Hitting a complex target: an update on interleukin-6 trans-signalling, Expert Opinion on Therapeutic Targets 16(2): 225-236 (2012).
Waetzig, G.H. et al., N-linked Glycosylation is essential for the stability but not the signaling function of the interleukin-6 signal transducer glycoprotein 130, Journal of Biological Chemistry, 285(3): 1781-1789 (2010).
Wahl et al., Improved Radioimaging and Tumor Localization with Monoclonal F(ab')2, J. of Nuclear Medicine, 24:316-325 (1983).
Waldmann et al., Metabolism of Immunoglobulins, Progr. Allergy, 13:1-110 (1969).
Ward et al., Influence of Interleukins-6 (IL-6) Dimerization of Formation of the High Affinity Hexameric IL-6 Receptor Complex, J. of Bio. Chem., 271(33):20138-20144 (1996).
Wells et al., Perspectives in Biochemistry: Additivity of Mutational Effects in Proteins, Biochem., 29(37):8509-8517 (1990).
Wigler et al., Transfer of Purified Herpes Virus Thymidine Kinase Gene to Cultured Mouse Cells, Cell 11:223-232 (1977).
Wigler et al., Transformation of mammalian cells with an amplifiable dominant-acting gene, Proc. Natl. Acad. Sci., 77(6):3567-3570 (1980).
Wildt et al., The Humanization of N-Glycosylation Pathways in Yeast, Nature Reviews, 3:119-128 (2005).
Wines et al., The IgG Fc Contains Distinc Fc Receptor (FcR) Binding Sites: The Leukocyte Receptors FcγRIIIa Bind to a Region in the Fc Distinct from that Recognized by Neonatal FcR and Protein A1, Jr. of Immunology, 164:5313-5318 (2000).
Winter et al., The Expression of Heat Shock Protein and Cognate Genes During Plant Development, Results and Problems in Cell Differentiation, pp. 85-105 (1991).
Woodle et al., Phase I Trial of Humanized, Fc Receptor nonbinding OKT3 Antibody huOKT3γ1(Ala-Ala) in the treatment of acute renal allograft rejection, Transplantation, 68(5):608-616 (1999).
Wright et al., Effect of glycosylation on antibody function: implications for genetic engineering, TibTech., 15:28-32 (1997).
Written Opinion for PCT/IB2015/002459, 5 pages (dated May 11, 2016).
Written Opinion for PCT/NL2015/050837, 7 pages (dated Jun. 2, 2016).
Yoshizaki et al., Interleukin-6 in autoimmune disorders, Semin. Immunol., 4:155-166 (1992).
Youngster et al., Structure Biology and Therapeutic Implications of Pegylated Interferon Alpha-2b, Current Pharmaceutical Design, 8:2139-2157 (2002).
Luig, M. et al, Inflammation-Induced IL-6 Functions as a Natural Brake on Macrophages and Limits GN, J. Am. Soc. Nephrol., 26: 1597-1607 (2015).
Scheller, J. et al, Interleukin-6: From basic biology to selective blockade of pro-inflammatory activities, Seminars in Immunology, 26: 2-12 (2014).
Chinese First Office Action issued in CN 201580075096.0 dated Apr. 30, 2020 (translated) 10 pages.
Chung, C. H. et al, Cetuximab-Induced Anaphylaxis and IgE Specific for Galactose-α-1,3-Galactose, The New England Journal of Medicine, 358(11): 1109-1117 (2008).
Huizinga, T. W. J. et al., Sarilumab, a fully human monoclonal antibody against IL-6Ra in patients with rheumatoid arthritis and an inadequate response to methotrexate: efficacy and safety results from the randomized, SARIL-RA-MOBILITY Part A trial, Annals of the Rheumatic Diseases, British Medical Association, 73:1626 — 1634 (2019).
Thanarajasingam, U and Niewold, T. B., Sirukumab: a novel therapy for lupus nephritis?, Expert Opinion on Investigational Drugs, 23(10):1744-7658 (2014).
Zhang, J., Drug Progression of Crohn's Disease, World Pharmacy: fascicule of synthetic drugs, biochemistry drugs, formulations, 13(3):148-150 (2020). [Cited in Chinese First Office Action issued in CN 201580075096.0, dated Apr. 30, 2020 and described on p. 9].
Blanchard, O. L. and Smoliga, J. M., Translating dosages from animal models to human clinical trials—revisiting body surface area scaling, The FASEB Journal, 29(5):1629-1634 (2015).
Van Norman, G., Limitations of Animal Studies for Predicting Toxicity in Clinical Trials, JACC: Basic to Translational Science, 4(7):845-854 (2019).
Demetris, A. J., Biliary wound healing, ductular reactions, and IL-6/gp130 signaling in the development of liver disease, World J. Gastroenterol, 12(22):3512-3522 (2006).
Garbers, C. et al., Interleukin-6: designing specific therapeutics for a complex cytokine, Nature Reviews, 17:395-412 (2018).
Mach, F. et al., 2019 ESC/EAS Guidelines for the management of dyslipidaemias: lipid modification to reduce cardiovascular risk, ESC, 41:111-188 (2020).
Melton, L. and Coombs, A., Actemra poised to launch IL-6 inhibitors, Nature Biotechnology, 26(9):957-959 (2008).
Ridker, P. M., From C-Reactive Protein to Interleukin-6 to Interleukin-1, Moving Upstream to Identify Novel Targets for Atheroprotection, Circulation Research, 145-156 (2016).
Swerdlow, D. et al., The interleukin-6 receptor as a target for prevention of coronary heart disease: a mendelian randomisation analysis, The Lancet, 379:1214-1224 (2012).

\* cited by examiner

```
2161  cctcaggtgtacacactgccctccatctaggaggagatgaccaagaatcaggtgtccctgaccctgtgtgaaccgcttctacccttct
 721  ·P··Q··V··Y··T··L··P··P··S··R··E··E··M··T··K··N··Q··V··S··L··T··C··L··V··K··G··F··Y··P··S·

2251  gatatcgctgtggagtggaatctaatgccagcccgaacaattacaagaccccctgtgctggattcctgacgtcctcttcttc
 751  ·D··I··A··V··E··W··E··S··N··G··Q··P··E··N··N··Y··K··T··T··P··V··L··D··S··D··G··S··F··F·

2341  ctgtactccaaactgaccgtggacaagtctagatggcagcaggggcaacgtgttctctgttccgtgatgcacgagcctgcacaatcac
 781  ·L··Y··S··K··L··T··V··D··K··S··R··W··Q··Q··G··N··V··F··S··C··S··V··M··H··E··A··L··H··N··H·

2431  tatacccagaagtccctgtctctgtctcctggcaag
 811  ·Y··T··Q··K··S··L··S··L··S··P··G··K·
```

FIG. 7 Continued

Fragment: CMV IE Promoter
Source: Cytomegalovirus
Plasmid Location: 37-620
Function: Mammalian expression promoter
Sequence:

ATTAATAGTAATCAATTACGGGGTCATTAGTTCATAGCCCATATATGGAGTTCCGCGTTACATAACTTA
CGGTAAATGGCCCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCAATGACGGTAAATGGC
CCGCCTGGCATTATGCCCAGTACATGACCTTATGGGACTTTCCTACTTGGCAGTACATCTACGTATTAG
TCATCGCTATTACCATGGTGATGCGGTTTTGGCAGTACATCAATGGGCGTGGATAGCGGTTTGACTCAC
GGGGATTTCCAAGTCTCCACCCCATTGACGTCAATGGGAGTTTGTTTTGGCACCAAAATCAACGGGAC
TTTCCAAAATGTCGTAACAACTCCGCCCCATTGACGCAAATGGGCGGTAGGCGTGTACGGTGGGAGGT
CTATATAAGCAGAGCTCGTTTAGTGAACCGTCAGATC

FIG. 8A

Fragment: Human IgH Poly A
Source: Human
Plasmid Location: 3211-3537
Function: Polyadenylation sequence
Sequence:

GTGCCACGGCCGGCAAGCCCCCGCTCCCCGGGCTCTCGCGGTCGCACGAGGATGCTTGGCACGTACCC
CGTCTACATACTTCCCAGGCACCCAGCATGGAAATAAAGCACCCACCACTGCCCTGGGCCCCTGCGAG
ACTGTGATGGTTCTTTCCACGGGTCAGGCCGAGTCTGAGGCCTGAGTGGCATGAGGGAGGCAGAGTGG
GTCCCACTGTCCCCACACTGGCCCAGGCTGTGCAGGTGTGCCTGGGCCGCCTAGGGTGGGGCTCAGCC
AGGGGCTGCCCTCGGCAGGGTGGGGGATTTGCCAGCGTGGCCCTCCCTCCAGCAG

FIG. 8B

Fragment: Amp (bla) gene
Source: Originally sourced from Salmonella paratyphi
Plasmid Location: 4362-5222 (complementary strand)
Function: Bacterial resistance
Sequence:

TTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAATGCCGCAA
AAAAGGGAATAAGGGCGACACGGAAATGTTGAATACTCAT

FIG. 8C

Fragment: SV40 Promoter
Source: Simian Virus 40
Plasmid Location: 5406-5761
Function: Mammalian expression promoter
Sequence:

```
CACGAGGCCCTATTGATTATTGACTAGCTAGTGTGGAATGTGTGTCAGTTAGGGTGTGGAAAGTCCCC
AGGCTCCCCAGCAGGCAGAAGTATGCAAAGCATGCATCTCAATTAGTCAGCAACCAGGTGTGGAAAG
TCCCCAGGCTCCCCAGCAGGCAGAAGTATGCAAAGCATGCATCTCAATTAGTCAGCAACCATAGTCCC
GCCCCTAACTCCGCCCATCCCGCCCCTAACTCCGCCCAGTTCCGCCCATTCTCCGCCCCATGGCTGACT
AATTTTTTTTATTTATGCAGAGGCCGAGGCCGCCTCGGCCTCTGAGCTATTCCAGAAGTAGTGAGGAG
GCTTTTTTTGGAGGCCT
```

FIG. 8D

Fragment: Dihydrofolate Reductase Coding Sequence
Source: Cytomegalovirus
Plasmid Location: 5794-6357
Function: Selection in CHO dhfr-cells
Sequence:

```
ATGGTTCGACCATTGAACTGCATCGTCGCCGTGTCCCAAAATATGGGGATTGGCAAGAACGGAGACCG
ACCCTGGCCTCCGCTCAGGAACGAGTTCAAGTACTTCCAAAGAATGACCACAACCTCTTCAGTGGAAG
GTAAACAGAATCTGGTGATTATGGGTAGGAAAACCTGGTTCTCCATTCCTGAGAAGAATCGACCTTTA
AAGGACAGAATTAATATAGTTCTCAGTAGAGAACTCAAAGAACCACCACGAGGAGCTCATTTTCTTGC
CAAAAGTTTGGATGATGCCTTAAGACTTATTGAACAACCGGAATTGGCAAGTAAAGTAGACATGGTTT
GGATAGTCGGAGGCAGTTCTGTTTACCAGGAAGCCATGAATCAACCAGGCCACCTCAGACTCTTTGTG
ACAAGGATCATGCAGGAATTTGAAAGTGACACGTTTTTCCCAGAAATTGATTTGGGGAAATATAAACT
TCTCCCAGAATACCCAGGCGTCCTCTCTGAGGTCCAGGAGGAAAAAGGCATCAAGTATAAGTTTGAAG
TCTACGAGAAGAAAGACTAA
```

FIG. 8E

Fragment: SV40 Poly
Source: Simian Virus 40
Plasmid Location: 6358-6680
Function: Polyadenylation sequence
Sequence:

```
CAGGAAGATGCTTTCAAGTTCTCTGCTCCCCTCCTAAAGCTATGCATTTTTATAAGACCATGGGACTTT
TGCTGGCTTTAGATCATAATCAGCCATACCACATTTGTAGAGGTTTTACTTGCTTTAAAAAACCTCCCA
CACCTCCCCCTGAACCTGAAACATAAAATGAATGCAATTGTTGTTGTTAACTTGTTTATTGCAGCTTCT
AATGGTTACAAATAAAGCAATAGCATCACAAATTTCACAAATAAAGCATTTTTTTCACTGCATTCTAGT
TGTGGTTTGTCCAAACTCATCAATGTATCTTATCATGTCTGGATCGG
```

FIG. 8F

SEQUENCE LISTING

```
<160> NUMBER OF SEQ ID NOS: 15

<210> SEQ ID NO 1
<211> LENGTH: 822
<212> TYPE: PRT
<213> ORGANISM: Artificial Sequence
<220> FEATURE:
<223> OTHER INFORMATION: gp130-Fc fusion monomer
```

-continued

```
<400> SEQUENCE: 1

Glu Leu Leu Asp Pro Cys Gly Tyr Ile Ser Pro Glu Ser Pro Val Val
1               5                   10                  15

Gln Leu His Ser Asn Phe Thr Ala Val Cys Val Leu Lys Glu Lys Cys
            20                  25                  30

Met Asp Tyr Phe His Val Asn Ala Asn Tyr Ile Val Trp Lys Thr Asn
        35                  40                  45

His Phe Thr Ile Pro Lys Glu Gln Tyr Thr Ile Ile Asn Arg Thr Ala
    50                  55                  60

Ser Ser Val Thr Phe Thr Asp Ile Ala Ser Leu Asn Ile Gln Leu Thr
65                  70                  75                  80

Cys Asn Ile Leu Thr Phe Gly Gln Leu Glu Gln Asn Val Tyr Gly Ile
                85                  90                  95

Thr Ile Ile Ser Gly Leu Pro Pro Glu Lys Pro Lys Asn Leu Ser Cys
            100                 105                 110

Ile Val Asn Glu Gly Lys Lys Met Arg Cys Glu Trp Asp Gly Gly Arg
        115                 120                 125

Glu Thr His Leu Glu Thr Asn Phe Thr Leu Lys Ser Glu Trp Ala Thr
130                 135                 140

His Lys Phe Ala Asp Cys Lys Ala Lys Arg Asp Thr Pro Thr Ser Cys
145                 150                 155                 160

Thr Val Asp Tyr Ser Thr Val Tyr Phe Val Asn Ile Glu Val Trp Val
                165                 170                 175

Glu Ala Glu Asn Ala Leu Gly Lys Val Thr Ser Asp His Ile Asn Phe
            180                 185                 190

Asp Pro Val Tyr Lys Val Lys Pro Asn Pro Pro His Asn Leu Ser Val
        195                 200                 205

Ile Asn Ser Glu Glu Leu Ser Ser Ile Leu Lys Leu Thr Trp Thr Asn
    210                 215                 220

Pro Ser Ile Lys Ser Val Ile Ile Leu Lys Tyr Asn Ile Gln Tyr Arg
225                 230                 235                 240

Thr Lys Asp Ala Ser Thr Trp Ser Gln Ile Pro Pro Glu Asp Thr Ala
                245                 250                 255

Ser Thr Arg Ser Ser Phe Thr Val Gln Asp Leu Lys Pro Phe Thr Glu
            260                 265                 270

Tyr Val Phe Arg Ile Arg Cys Met Lys Glu Asp Gly Lys Gly Tyr Trp
        275                 280                 285

Ser Asp Trp Ser Glu Glu Ala Ser Gly Ile Thr Tyr Glu Asp Arg Pro
    290                 295                 300

Ser Lys Ala Pro Ser Phe Trp Tyr Lys Ile Asp Pro Ser His Thr Gln
305                 310                 315                 320

Gly Tyr Arg Thr Val Gln Leu Val Trp Lys Thr Leu Pro Pro Phe Glu
                325                 330                 335

Ala Asn Gly Lys Ile Leu Asp Tyr Glu Val Thr Leu Thr Arg Trp Lys
            340                 345                 350

Ser His Leu Gln Asn Tyr Thr Val Asn Ala Thr Lys Leu Thr Val Asn
        355                 360                 365

Leu Thr Asn Asp Arg Tyr Leu Ala Thr Leu Thr Val Arg Asn Leu Val
    370                 375                 380

Gly Lys Ser Asp Ala Ala Val Leu Thr Ile Pro Ala Cys Asp Phe Gln
385                 390                 395                 400

Ala Thr His Pro Val Met Asp Leu Lys Ala Phe Pro Lys Asp Asn Met
```

-continued

```
                405                 410                 415
Leu Trp Val Glu Trp Thr Thr Pro Arg Glu Ser Val Lys Lys Tyr Ile
            420                 425                 430
Leu Glu Trp Cys Val Leu Ser Asp Lys Ala Pro Cys Ile Thr Asp Trp
            435                 440                 445
Gln Gln Glu Asp Gly Thr Val His Arg Thr Tyr Leu Arg Gly Asn Leu
    450                 455                 460
Ala Glu Ser Lys Cys Tyr Leu Ile Thr Val Thr Pro Val Tyr Ala Asp
465                 470                 475                 480
Gly Pro Gly Ser Pro Glu Ser Ile Lys Ala Tyr Leu Lys Gln Ala Pro
                485                 490                 495
Pro Ser Lys Gly Pro Thr Val Arg Thr Lys Lys Val Gly Lys Asn Glu
            500                 505                 510
Ala Val Leu Glu Trp Asp Gln Leu Pro Val Asp Val Gln Asn Gly Phe
            515                 520                 525
Ile Arg Asn Tyr Thr Ile Phe Tyr Arg Thr Ile Ile Gly Asn Glu Thr
        530                 535                 540
Ala Val Asn Val Asp Ser Ser His Thr Glu Tyr Thr Leu Ser Ser Leu
545                 550                 555                 560
Thr Ser Asp Thr Leu Tyr Met Val Arg Met Ala Ala Tyr Thr Asp Glu
                565                 570                 575
Gly Gly Lys Asp Gly Pro Glu Phe Thr Phe Thr Thr Pro Lys Phe Ala
            580                 585                 590
Gln Gly Glu Asp Lys Thr His Thr Cys Pro Pro Cys Pro Ala Pro Glu
        595                 600                 605
Ala Glu Gly Ala Pro Ser Val Phe Leu Phe Pro Pro Lys Pro Lys Asp
    610                 615                 620
Thr Leu Met Ile Ser Arg Thr Pro Glu Val Thr Cys Val Val Val Asp
625                 630                 635                 640
Val Ser His Glu Asp Pro Glu Val Lys Phe Asn Trp Tyr Val Asp Gly
                645                 650                 655
Val Glu Val His Asn Ala Lys Thr Lys Pro Arg Glu Glu Gln Tyr Asn
            660                 665                 670
Ser Thr Tyr Arg Val Val Ser Val Leu Thr Val Leu His Gln Asp Trp
        675                 680                 685
Leu Asn Gly Lys Glu Tyr Lys Cys Lys Val Ser Asn Lys Ala Leu Pro
    690                 695                 700
Ala Pro Ile Glu Lys Thr Ile Ser Lys Ala Lys Gly Gln Pro Arg Glu
705                 710                 715                 720
Pro Gln Val Tyr Thr Leu Pro Pro Ser Arg Glu Glu Met Thr Lys Asn
                725                 730                 735
Gln Val Ser Leu Thr Cys Leu Val Lys Gly Phe Tyr Pro Ser Asp Ile
            740                 745                 750
Ala Val Glu Trp Glu Ser Asn Gly Gln Pro Glu Asn Asn Tyr Lys Thr
        755                 760                 765
Thr Pro Pro Val Leu Asp Ser Asp Gly Ser Phe Phe Leu Tyr Ser Lys
    770                 775                 780
Leu Thr Val Asp Lys Ser Arg Trp Gln Gln Gly Asn Val Phe Ser Cys
785                 790                 795                 800
Ser Val Met His Glu Ala Leu His Asn His Tyr Thr Gln Lys Ser Leu
                805                 810                 815
Ser Leu Ser Pro Gly Lys
            820
```

<210> SEQ ID NO 2
<211> LENGTH: 844
<212> TYPE: PRT
<213> ORGANISM: Artificial Sequence
<220> FEATURE:
<223> OTHER INFORMATION: gp130-Fc fusion monomer with endogenous signal peptide

<400> SEQUENCE: 2

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
```

-continued

```
               355                 360                 365
Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Asp Lys Thr His Thr Cys Pro
    610                 615                 620

Pro Cys Pro Ala Pro Glu Ala Glu Gly Ala Pro Ser Val Phe Leu Phe
625                 630                 635                 640

Pro Pro Lys Pro Lys Asp Thr Leu Met Ile Ser Arg Thr Pro Glu Val
                645                 650                 655

Thr Cys Val Val Val Asp Val Ser His Glu Asp Pro Glu Val Lys Phe
            660                 665                 670

Asn Trp Tyr Val Asp Gly Val Glu Val His Asn Ala Lys Thr Lys Pro
        675                 680                 685

Arg Glu Glu Gln Tyr Asn Ser Thr Tyr Arg Val Val Ser Val Leu Thr
    690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
            740                 745                 750

Glu Glu Met Thr Lys Asn Gln Val Ser Leu Thr Cys Leu Val Lys Gly
        755                 760                 765

Phe Tyr Pro Ser Asp Ile Ala Val Glu Trp Glu Ser Asn Gly Gln Pro
    770                 775                 780
```

```
Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
            805                 810                 815

Gly Asn Val Phe Ser Cys Ser Val Met His Glu Ala Leu His Asn His
        820                 825                 830

Tyr Thr Gln Lys Ser Leu Ser Leu Ser Pro Gly Lys
        835                 840

<210> SEQ ID NO 3
<211> LENGTH: 11
<212> TYPE: PRT
<213> ORGANISM: Artificial Sequence
<220> FEATURE:
<223> OTHER INFORMATION: gp130 D6 domain

<400> SEQUENCE: 3

Thr Phe Thr Thr Pro Lys Phe Ala Gln Gly Glu
1               5                   10

<210> SEQ ID NO 4
<211> LENGTH: 4
<212> TYPE: PRT
<213> ORGANISM: Artificial Sequence
<220> FEATURE:
<223> OTHER INFORMATION: gp130 D6 domain

<400> SEQUENCE: 4

Ala Glu Gly Ala
1

<210> SEQ ID NO 5
<211> LENGTH: 4
<212> TYPE: PRT
<213> ORGANISM: Artificial Sequence
<220> FEATURE:
<223> OTHER INFORMATION: IgG1 sequence

<400> SEQUENCE: 5

Cys Pro Pro Cys
1

<210> SEQ ID NO 6
<211> LENGTH: 44
<212> TYPE: DNA
<213> ORGANISM: Artificial Sequence
<220> FEATURE:
<223> OTHER INFORMATION: primer OL1425

<400> SEQUENCE: 6
ctgttgctac gcgtgtccac tccgagctgc tggatccttg cggc              44

<210> SEQ ID NO 7
<211> LENGTH: 48
<212> TYPE: DNA
<213> ORGANISM: Artificial Sequence
<220> FEATURE:
<223> OTHER INFORMATION: primer OL1426

<400> SEQUENCE: 7
gcgggggctt gccggccgtg gcactcactt gccaggagac agagacag          48

<210> SEQ ID NO 8
<211> LENGTH: 2466
```

<212> TYPE: DNA
<213> ORGANISM: Artificial Sequence
<220> FEATURE:
<223> OTHER INFORMATION: single gp130-Fc subunit
<220> FEATURE:
<221> NAME/KEY: CDS
<222> LOCATION: (1)..(2466)

<400> SEQUENCE: 8

| | | | | | | | | | | | | | | | | |
|---|---|---|---|---|---|---|---|---|---|---|---|---|---|---|---|---|
| gag | ctg | ctg | gat | cct | tgc | ggc | tat | atc | tcc | cct | gag | tct | cct | gtg | gtg | 48 |
| Glu | Leu | Leu | Asp | Pro | Cys | Gly | Tyr | Ile | Ser | Pro | Glu | Ser | Pro | Val | Val | |
| 1 | | | | 5 | | | | | 10 | | | | | 15 | | |
| cag | ctg | cat | tct | aac | ttc | acc | gcc | gtg | tgt | gtg | ctg | aag | gaa | aag | tgc | 96 |
| Gln | Leu | His | Ser | Asn | Phe | Thr | Ala | Val | Cys | Val | Leu | Lys | Glu | Lys | Cys | |
| | | | 20 | | | | | 25 | | | | | 30 | | | |
| atg | gac | tac | ttc | cac | gtg | aac | gcc | aac | tac | atc | gtg | tgg | aaa | acc | aac | 144 |
| Met | Asp | Tyr | Phe | His | Val | Asn | Ala | Asn | Tyr | Ile | Val | Trp | Lys | Thr | Asn | |
| | | 35 | | | | | 40 | | | | | 45 | | | | |
| cac | ttc | acc | atc | ccc | aag | gag | cag | tac | acc | atc | atc | aac | cgg | acc | gct | 192 |
| His | Phe | Thr | Ile | Pro | Lys | Glu | Gln | Tyr | Thr | Ile | Ile | Asn | Arg | Thr | Ala | |
| | 50 | | | | | 55 | | | | | 60 | | | | | |
| tct | tct | gtg | acc | ttc | acc | gat | atc | gcc | tcc | ctg | aat | atc | cag | ctg | acc | 240 |
| Ser | Ser | Val | Thr | Phe | Thr | Asp | Ile | Ala | Ser | Leu | Asn | Ile | Gln | Leu | Thr | |
| 65 | | | | | 70 | | | | | 75 | | | | | 80 | |
| tgc | aac | atc | ctg | acc | ttt | gga | cag | ctg | gag | cag | aat | gtg | tac | ggc | atc | 288 |
| Cys | Asn | Ile | Leu | Thr | Phe | Gly | Gln | Leu | Glu | Gln | Asn | Val | Tyr | Gly | Ile | |
| | | | | 85 | | | | | 90 | | | | | 95 | | |
| acc | atc | atc | tct | ggc | ctg | cct | cca | gag | aag | cct | aag | aac | ctg | tcc | tgc | 336 |
| Thr | Ile | Ile | Ser | Gly | Leu | Pro | Pro | Glu | Lys | Pro | Lys | Asn | Leu | Ser | Cys | |
| | | | 100 | | | | | 105 | | | | | 110 | | | |
| atc | gtg | aat | gag | ggc | aag | aag | atg | agg | tgt | gag | tgg | gat | ggc | ggc | aga | 384 |
| Ile | Val | Asn | Glu | Gly | Lys | Lys | Met | Arg | Cys | Glu | Trp | Asp | Gly | Gly | Arg | |
| | | 115 | | | | | 120 | | | | | 125 | | | | |
| gag | aca | cat | ctg | gag | acc | aac | ttc | acc | ctg | aag | tct | gag | tgg | gcc | acc | 432 |
| Glu | Thr | His | Leu | Glu | Thr | Asn | Phe | Thr | Leu | Lys | Ser | Glu | Trp | Ala | Thr | |
| | 130 | | | | | 135 | | | | | 140 | | | | | |
| cac | aag | ttt | gcc | gac | tgc | aag | gcc | aag | aga | gat | acc | cct | acc | tct | tgc | 480 |
| His | Lys | Phe | Ala | Asp | Cys | Lys | Ala | Lys | Arg | Asp | Thr | Pro | Thr | Ser | Cys | |
| 145 | | | | | 150 | | | | | 155 | | | | | 160 | |
| acc | gtg | gac | tac | tcc | acc | gtg | tac | ttc | gtg | aac | atc | gag | gtg | tgg | gtg | 528 |
| Thr | Val | Asp | Tyr | Ser | Thr | Val | Tyr | Phe | Val | Asn | Ile | Glu | Val | Trp | Val | |
| | | | | 165 | | | | | 170 | | | | | 175 | | |
| gag | gct | gag | aat | gct | ctg | ggc | aag | gtg | acc | tct | gac | cac | atc | aac | ttc | 576 |
| Glu | Ala | Glu | Asn | Ala | Leu | Gly | Lys | Val | Thr | Ser | Asp | His | Ile | Asn | Phe | |
| | | | 180 | | | | | 185 | | | | | 190 | | | |
| gac | ccc | gtg | tac | aag | gtg | aag | cct | aac | cct | cct | cac | aac | ctg | tcc | gtg | 624 |
| Asp | Pro | Val | Tyr | Lys | Val | Lys | Pro | Asn | Pro | Pro | His | Asn | Leu | Ser | Val | |
| | | 195 | | | | | 200 | | | | | 205 | | | | |
| atc | aac | tct | gag | gag | ctg | tcc | tct | atc | ctg | aag | ctg | acc | tgg | acc | aac | 672 |
| Ile | Asn | Ser | Glu | Glu | Leu | Ser | Ser | Ile | Leu | Lys | Leu | Thr | Trp | Thr | Asn | |
| | 210 | | | | | 215 | | | | | 220 | | | | | |
| cct | tcc | atc | aag | tcc | gtg | atc | atc | ctg | aag | tac | aac | atc | cag | tac | agg | 720 |
| Pro | Ser | Ile | Lys | Ser | Val | Ile | Ile | Leu | Lys | Tyr | Asn | Ile | Gln | Tyr | Arg | |
| 225 | | | | | 230 | | | | | 235 | | | | | 240 | |
| acc | aag | gat | gct | tct | acc | tgg | tct | cag | atc | cct | cct | gag | gat | acc | gct | 768 |
| Thr | Lys | Asp | Ala | Ser | Thr | Trp | Ser | Gln | Ile | Pro | Pro | Glu | Asp | Thr | Ala | |
| | | | | 245 | | | | | 250 | | | | | 255 | | |
| tcc | acc | aga | tcc | agc | ttc | aca | gtg | cag | gac | ctg | aag | cct | ttt | acc | gag | 816 |
| Ser | Thr | Arg | Ser | Ser | Phe | Thr | Val | Gln | Asp | Leu | Lys | Pro | Phe | Thr | Glu | |
| | | | 260 | | | | | 265 | | | | | 270 | | | |
| tac | gtg | ttc | agg | atc | cgg | tgc | atg | aag | gag | gat | ggc | aag | ggc | tat | tgg | 864 |

```
Tyr Val Phe Arg Ile Arg Cys Met Lys Glu Asp Gly Lys Gly Tyr Trp
            275                 280                 285 tct gac tgg tct gag gag gct tct ggc atc acc tac gag gac aga cct      912
Ser Asp Trp Ser Glu Glu Ala Ser Gly Ile Thr Tyr Glu Asp Arg Pro
        290                 295                 300 tct aag gcc cct agc ttc tgg tac aag atc gac cct tct cac acc cag      960
Ser Lys Ala Pro Ser Phe Trp Tyr Lys Ile Asp Pro Ser His Thr Gln
305                 310                 315                 320 ggc tat aga aca gtg cag ctg gtg tgg aaa acc ctg cct cca ttc gag     1008
Gly Tyr Arg Thr Val Gln Leu Val Trp Lys Thr Leu Pro Pro Phe Glu
                325                 330                 335 gct aat ggc aag atc ctg gac tat gag gtg acc ctg acc aga tgg aag     1056
Ala Asn Gly Lys Ile Leu Asp Tyr Glu Val Thr Leu Thr Arg Trp Lys
            340                 345                 350 tct cac ctg cag aac tac acc gtg aac gct acc aag ctg acc gtg aac     1104
Ser His Leu Gln Asn Tyr Thr Val Asn Ala Thr Lys Leu Thr Val Asn
        355                 360                 365 ctg acc aac gat aga tac ctg gct acc ctg acc gtg aga aat ctg gtg     1152
Leu Thr Asn Asp Arg Tyr Leu Ala Thr Leu Thr Val Arg Asn Leu Val
370                 375                 380 ggc aag tct gat gct gct gtg ctg acc atc cct gcc tgt gat ttt cag     1200
Gly Lys Ser Asp Ala Ala Val Leu Thr Ile Pro Ala Cys Asp Phe Gln
                385                 390                 395                 400 gct acc cac cct gtg atg gat ctg aag gcc ttc ccc aag gat aac atg     1248
Ala Thr His Pro Val Met Asp Leu Lys Ala Phe Pro Lys Asp Asn Met
                    405                 410                 415 ctg tgg gtg gag tgg aca aca cct aga gag tcc gtg aag aag tac atc     1296
Leu Trp Val Glu Trp Thr Thr Pro Arg Glu Ser Val Lys Lys Tyr Ile
                420                 425                 430 ctg gag tgg tgc gtg ctg tct gat aag gcc cct tgc atc aca gat tgg     1344
Leu Glu Trp Cys Val Leu Ser Asp Lys Ala Pro Cys Ile Thr Asp Trp
            435                 440                 445 cag cag gag gat ggc acc gtg cat aga acc tac ctg aga ggc aat ctg     1392
Gln Gln Glu Asp Gly Thr Val His Arg Thr Tyr Leu Arg Gly Asn Leu
        450                 455                 460 gcc gag tct aag tgc tat ctg atc acc gtg acc cct gtg tat gct gat     1440
Ala Glu Ser Lys Cys Tyr Leu Ile Thr Val Thr Pro Val Tyr Ala Asp
465                 470                 475                 480 gga cct ggc tct cct gag tct atc aag gcc tac ctg aag cag gct cct     1488
Gly Pro Gly Ser Pro Glu Ser Ile Lys Ala Tyr Leu Lys Gln Ala Pro
                485                 490                 495 cca tct aag gga cct acc gtg agg aca aag aag gtg ggc aag aac gag     1536
Pro Ser Lys Gly Pro Thr Val Arg Thr Lys Lys Val Gly Lys Asn Glu
                    500                 505                 510 gct gtg ctg gag tgg gat cag ctg cct gtg gat gtg cag aac ggc ttc     1584
Ala Val Leu Glu Trp Asp Gln Leu Pro Val Asp Val Gln Asn Gly Phe
                515                 520                 525 atc cgg aac tac acc atc ttc tac cgg acc atc atc ggc aat gag acc     1632
Ile Arg Asn Tyr Thr Ile Phe Tyr Arg Thr Ile Ile Gly Asn Glu Thr
        530                 535                 540 gcc gtg aac gtg gat tct tcc cac acc gag tac aca ctg tcc tct ctg     1680
Ala Val Asn Val Asp Ser Ser His Thr Glu Tyr Thr Leu Ser Ser Leu
545                 550                 555                 560 acc tct gac acc ctg tac atg gtg aga atg gcc gct tat acc gat gag     1728
Thr Ser Asp Thr Leu Tyr Met Val Arg Met Ala Ala Tyr Thr Asp Glu
                565                 570                 575 ggc ggc aag gat gga cct gag ttc acc ttc acc acc cct aag ttc gcc     1776
Gly Gly Lys Asp Gly Pro Glu Phe Thr Phe Thr Thr Pro Lys Phe Ala
                    580                 585                 590
```

| | | |
|---|---|---|
| cag ggc gag gac aag acc cac acc tgt cct cct tgt cct gct cct gag<br>Gln Gly Glu Asp Lys Thr His Thr Cys Pro Pro Cys Pro Ala Pro Glu<br>595                           600                    605 | | 1824 |
| gct gag ggc gct cct tct gtg ttt ctg ttc ccc cca aag cct aag gat<br>Ala Glu Gly Ala Pro Ser Val Phe Leu Phe Pro Pro Lys Pro Lys Asp<br>610                           615                    620 | | 1872 |
| acc ctg atg atc tcc aga acc cct gag gtg aca tgt gtg gtg gtg gat<br>Thr Leu Met Ile Ser Arg Thr Pro Glu Val Thr Cys Val Val Val Asp<br>625                           630                    635                    640 | | 1920 |
| gtg tct cat gag gac ccc gag gtg aag ttc aac tgg tac gtg gat ggc<br>Val Ser His Glu Asp Pro Glu Val Lys Phe Asn Trp Tyr Val Asp Gly<br>                        645                    650                    655 | | 1968 |
| gtg gag gtg cac aat gct aag acc aag cct agg gag gag cag tac aac<br>Val Glu Val His Asn Ala Lys Thr Lys Pro Arg Glu Glu Gln Tyr Asn<br>660                           665                    670 | | 2016 |
| tcc acc tac aga gtg gtg tct gtg ctg aca gtg ctg cat cag gat tgg<br>Ser Thr Tyr Arg Val Val Ser Val Leu Thr Val Leu His Gln Asp Trp<br>                        675                    680                    685 | | 2064 |
| ctg aac ggc aag gag tac aag tgc aag gtg tcc aac aag gct ctg cct<br>Leu Asn Gly Lys Glu Tyr Lys Cys Lys Val Ser Asn Lys Ala Leu Pro<br>690                           695                    700 | | 2112 |
| gct cct atc gaa aag acc atc tcc aag gct aag gga cag cct aga gag<br>Ala Pro Ile Glu Lys Thr Ile Ser Lys Ala Lys Gly Gln Pro Arg Glu<br>705                         710                    715                    720 | | 2160 |
| cct cag gtg tac aca ctg cct cca tct agg gag gag atg acc aag aat<br>Pro Gln Val Tyr Thr Leu Pro Pro Ser Arg Glu Glu Met Thr Lys Asn<br>                        725                    730                    735 | | 2208 |
| cag gtg tcc ctg acc tgt ctg gtg aag ggc ttc tac cct tct gat atc<br>Gln Val Ser Leu Thr Cys Leu Val Lys Gly Phe Tyr Pro Ser Asp Ile<br>740                           745                    750 | | 2256 |
| gct gtg gag tgg gag tct aat ggc cag ccc gag aac aat tac aag acc<br>Ala Val Glu Trp Glu Ser Asn Gly Gln Pro Glu Asn Asn Tyr Lys Thr<br>                        755                    760                    765 | | 2304 |
| acc cct cct gtg ctg gat tct gac ggc tcc ttc ttc ctg tac tcc aaa<br>Thr Pro Pro Val Leu Asp Ser Asp Gly Ser Phe Phe Leu Tyr Ser Lys<br>770                           775                    780 | | 2352 |
| ctg acc gtg gac aag tct aga tgg cag cag ggc aac gtg ttc tct tgt<br>Leu Thr Val Asp Lys Ser Arg Trp Gln Gln Gly Asn Val Phe Ser Cys<br>785                         790                    795                    800 | | 2400 |
| tcc gtg atg cac gag gct ctg cac aat cac tat acc cag aag tcc ctg<br>Ser Val Met His Glu Ala Leu His Asn His Tyr Thr Gln Lys Ser Leu<br>                        805                    810                    815 | | 2448 |
| tct ctg tct cct ggc aag<br>Ser Leu Ser Pro Gly Lys<br>          820 | | 2466 |

<210> SEQ ID NO 9
<211> LENGTH: 822
<212> TYPE: PRT
<213> ORGANISM: Artificial Sequence
<220> FEATURE:
<223> OTHER INFORMATION: Synthetic Construct

<400> SEQUENCE: 9

Glu Leu Leu Asp Pro Cys Gly Tyr Ile Ser Pro Glu Ser Pro Val Val
1                 5                    10                    15

Gln Leu His Ser Asn Phe Thr Ala Val Cys Val Leu Lys Glu Lys Cys
                 20                    25                    30

Met Asp Tyr Phe His Val Asn Ala Asn Tyr Ile Val Trp Lys Thr Asn
        35                    40                    45

```
His Phe Thr Ile Pro Lys Glu Gln Tyr Thr Ile Ile Asn Arg Thr Ala
 50                  55                  60
Ser Ser Val Thr Phe Thr Asp Ile Ala Ser Leu Asn Ile Gln Leu Thr
 65                  70                  75                  80
Cys Asn Ile Leu Thr Phe Gly Gln Leu Glu Gln Asn Val Tyr Gly Ile
                     85                  90                  95
Thr Ile Ile Ser Gly Leu Pro Pro Glu Lys Pro Lys Asn Leu Ser Cys
                100                 105                 110
Ile Val Asn Glu Gly Lys Lys Met Arg Cys Glu Trp Asp Gly Gly Arg
                115                 120                 125
Glu Thr His Leu Glu Thr Asn Phe Thr Leu Lys Ser Glu Trp Ala Thr
                130                 135                 140
His Lys Phe Ala Asp Cys Lys Ala Lys Arg Asp Thr Pro Thr Ser Cys
145                 150                 155                 160
Thr Val Asp Tyr Ser Thr Val Tyr Phe Val Asn Ile Glu Val Trp Val
                165                 170                 175
Glu Ala Glu Asn Ala Leu Gly Lys Val Thr Ser Asp His Ile Asn Phe
                180                 185                 190
Asp Pro Val Tyr Lys Val Lys Pro Asn Pro Pro His Asn Leu Ser Val
                195                 200                 205
Ile Asn Ser Glu Glu Leu Ser Ser Ile Leu Lys Leu Thr Trp Thr Asn
210                 215                 220
Pro Ser Ile Lys Ser Val Ile Ile Leu Lys Tyr Asn Ile Gln Tyr Arg
225                 230                 235                 240
Thr Lys Asp Ala Ser Thr Trp Ser Gln Ile Pro Pro Glu Asp Thr Ala
                245                 250                 255
Ser Thr Arg Ser Ser Phe Thr Val Gln Asp Leu Lys Pro Phe Thr Glu
                260                 265                 270
Tyr Val Phe Arg Ile Arg Cys Met Lys Glu Asp Gly Lys Gly Tyr Trp
                275                 280                 285
Ser Asp Trp Ser Glu Glu Ala Ser Gly Ile Thr Tyr Glu Asp Arg Pro
290                 295                 300
Ser Lys Ala Pro Ser Phe Trp Tyr Lys Ile Asp Pro Ser His Thr Gln
305                 310                 315                 320
Gly Tyr Arg Thr Val Gln Leu Val Trp Lys Thr Leu Pro Pro Phe Glu
                325                 330                 335
Ala Asn Gly Lys Ile Leu Asp Tyr Glu Val Thr Leu Thr Arg Trp Lys
                340                 345                 350
Ser His Leu Gln Asn Tyr Thr Val Asn Ala Thr Lys Leu Thr Val Asn
                355                 360                 365
Leu Thr Asn Asp Arg Tyr Leu Ala Thr Leu Thr Val Arg Asn Leu Val
370                 375                 380
Gly Lys Ser Asp Ala Ala Val Leu Thr Ile Pro Ala Cys Asp Phe Gln
385                 390                 395                 400
Ala Thr His Pro Val Met Asp Leu Lys Ala Phe Pro Lys Asp Asn Met
                405                 410                 415
Leu Trp Val Glu Trp Thr Thr Pro Arg Glu Ser Val Lys Lys Tyr Ile
                420                 425                 430
Leu Glu Trp Cys Val Leu Ser Asp Lys Ala Pro Cys Ile Thr Asp Trp
                435                 440                 445
Gln Gln Glu Asp Gly Thr Val His Arg Thr Tyr Leu Arg Gly Asn Leu
450                 455                 460
Ala Glu Ser Lys Cys Tyr Leu Ile Thr Val Thr Pro Val Tyr Ala Asp
```

Gly Pro Gly Ser Pro Glu Ser Ile Lys Ala Tyr Leu Lys Gln Ala Pro
465                 470                 475                 480

Pro Ser Lys Gly Pro Thr Val Arg Thr Lys Val Gly Lys Asn Glu
            485                 490                 495

Ala Val Leu Glu Trp Asp Gln Leu Pro Val Asp Val Gln Asn Gly Phe
                500                 505                 510

Ile Arg Asn Tyr Thr Ile Phe Tyr Arg Thr Ile Ile Gly Asn Glu Thr
            515                 520                 525

Ala Val Asn Val Asp Ser Ser His Thr Glu Tyr Thr Leu Ser Ser Leu
530                 535                 540

Thr Ser Asp Thr Leu Tyr Met Val Arg Met Ala Ala Tyr Thr Asp Glu
545                 550                 555                 560

Gly Gly Lys Asp Gly Pro Glu Phe Thr Phe Thr Thr Pro Lys Phe Ala
                565                 570                 575

Gln Gly Glu Asp Lys Thr His Thr Cys Pro Pro Cys Pro Ala Pro Glu
            580                 585                 590

Ala Glu Gly Ala Pro Ser Val Phe Leu Phe Pro Pro Lys Pro Lys Asp
        595                 600                 605

Thr Leu Met Ile Ser Arg Thr Pro Glu Val Thr Cys Val Val Val Asp
610                 615                 620

Val Ser His Glu Asp Pro Glu Val Lys Phe Asn Trp Tyr Val Asp Gly
625                 630                 635                 640

Val Glu Val His Asn Ala Lys Thr Lys Pro Arg Glu Glu Gln Tyr Asn
                645                 650                 655

Ser Thr Tyr Arg Val Val Ser Val Leu Thr Val Leu His Gln Asp Trp
            660                 665                 670

Leu Asn Gly Lys Glu Tyr Lys Cys Lys Val Ser Asn Lys Ala Leu Pro
        675                 680                 685

Ala Pro Ile Glu Lys Thr Ile Ser Lys Ala Lys Gly Gln Pro Arg Glu
690                 695                 700

Pro Gln Val Tyr Thr Leu Pro Pro Ser Arg Glu Glu Met Thr Lys Asn
705                 710                 715                 720

Gln Val Ser Leu Thr Cys Leu Val Lys Gly Phe Tyr Pro Ser Asp Ile
                725                 730                 735

Ala Val Glu Trp Glu Ser Asn Gly Gln Pro Glu Asn Asn Tyr Lys Thr
            740                 745                 750

Thr Pro Pro Val Leu Asp Ser Asp Gly Ser Phe Phe Leu Tyr Ser Lys
        755                 760                 765

Leu Thr Val Asp Lys Ser Arg Trp Gln Gln Gly Asn Val Phe Ser Cys
770                 775                 780

Ser Val Met His Glu Ala Leu His Asn His Tyr Thr Gln Lys Ser Leu
785                 790                 795                 800

Ser Leu Ser Pro Gly Lys
                805                 810                 815

820

<210> SEQ ID NO 10
<211> LENGTH: 584
<212> TYPE: DNA
<213> ORGANISM: Artificial Sequence
<220> FEATURE:
<223> OTHER INFORMATION: CMV IE Promoter

<400> SEQUENCE: 10
attaatagta atcaattacg gggtcattag ttcatagccc atatatggag ttccgcgtta    60

```
cataacttac ggtaaatggc ccgcctggct gaccgcccaa cgaccccccgc ccattgacgt    120 caataatgac gtatgttccc atagtaacgc caataggact tttccattga cgtcaatggg    180
tggagtattt acggtaaact gcccacttgg cagtacatca agtgtatcat atgccaagta    240
cgccccctat tgacgtcaat gacggtaaat ggcccgcctg gcattatgcc cagtacatga    300
ccttatggga ctttcctact tggcagtaca tctacgtatt agtcatcgct attaccatgg    360
tgatgcggtt ttggcagtac atcaatgggc gtggatagcg gtttgactca cggggatttc    420
caagtctcca ccccattgac gtcaatggga gtttgttttg gcaccaaaat caacgggact    480
ttccaaaatg tcgtaacaac tccgccccat tgacgcaaat gggcggtagg cgtgtacggt    540
gggaggtcta taagcaga gctcgtttag tgaaccgtca gatc                      584
```

```
<210> SEQ ID NO 11
<211> LENGTH: 327
<212> TYPE: DNA
<213> ORGANISM: Artificial Sequence
<220> FEATURE:
<223> OTHER INFORMATION: Human IgH Poly A

<400> SEQUENCE: 11
gtgccacggc cggcaagccc ccgctccccg ggctctcgcg gtcgcacgag gatgcttggc     60
acgtaccccg tctacatact tcccaggcac ccagcatgga aataaagcac ccaccactgc    120
cctgggcccc tgcgagactg tgatggttct ttccacgggt caggccgagt ctgaggcctg    180
agtggcatga gggaggcaga gtgggtccca ctgtccccac actggcccag ctgtgcagg     240 tgtgcctggg ccgcctaggg tggggctcag ccaggggctg ccctcggcag ggtggggat    300 ttgccagcgt ggccctccct ccagcag                                       327
```

```
<210> SEQ ID NO 12
<211> LENGTH: 861
<212> TYPE: DNA
<213> ORGANISM: Artificial Sequence
<220> FEATURE:
<223> OTHER INFORMATION: Amp (bla) gene

<400> SEQUENCE: 12
ttaccaatgc ttaatcagtg aggcacctat ctcagcgatc tgtctatttc gttcatccat     60
agttgcctga ctccccgtcg tgtagataac tacgatacgg gagggcttac catctggccc    120
cagtgctgca atgataccgc gagacccacg ctcaccggct ccagatttat cagcaataaa    180
ccagccagcc ggaagggccg agcgcagaag tggtcctgca actttatccg cctccatcca    240
gtctattaat tgttgccggg aagctagagt aagtagttcg ccagttaata gtttgcgcaa    300
cgttgttgcc attgctacag gcatcgtggt gtcacgctcg tcgtttggta tggcttcatt    360
cagctccggt tcccaacgat caaggcgagt tacatgatcc cccatgttgt gcaaaaaagc    420
ggttagctcc ttcggtcctc cgatcgttgt cagaagtaag ttggccgcag tgttatcact    480
catggttatg gcagcactgc ataattctct tactgtcatg ccatccgtaa gatgcttttc    540
tgtgactggt gagtactcaa ccaagtcatt ctgagaatag tgtatgcggc gaccgagttg    600
ctcttgcccg gcgtcaatac gggataatac cgcgccacat agcagaactt taaaagtgct    660
catcattgga aaacgttctt cggggcgaaa actctcaagg atcttaccgc tgttgagatc    720
cagttcgatg taacccactc gtgcacccaa ctgatcttca gcatctttta ctttcaccag    780
cgtttctggg tgagcaaaaa caggaaggca aaatgccgca aaaaagggaa taagggcgac    840
```
acggaaatgt tgaatactca t                                              861

<210> SEQ ID NO 13
<211> LENGTH: 356
<212> TYPE: DNA
<213> ORGANISM: Artificial Sequence
<220> FEATURE:
<223> OTHER INFORMATION: SV40 Promoter

<400> SEQUENCE: 13
cacgaggccc tattgattat tgactagcta gtgtggaatg tgtgtcagtt agggtgtgga     60
aagtccccag gctccccagc aggcagaagt atgcaaagca tgcatctcaa ttagtcagca    120
accaggtgtg gaaagtcccc aggctcccca gcaggcagaa gtatgcaaag catgcatctc    180
aattagtcag caaccatagt cccgcccta actccgccca tcccgcccct aactccgccc     240
agttccgccc attctccgcc ccatggctga ctaattttt ttatttatgc agaggccgag     300
gccgcctcgg cctctgagct attccagaag tagtgaggag gcttttttgg aggcct        356

<210> SEQ ID NO 14
<211> LENGTH: 564
<212> TYPE: DNA
<213> ORGANISM: Artificial Sequence
<220> FEATURE:
<223> OTHER INFORMATION: Dihydrofolate Reductase Coding Sequence

<400> SEQUENCE: 14
atggttcgac cattgaactg catcgtcgcc gtgtcccaaa atatggggat tggcaagaac     60
ggagaccgac cctggcctcc gctcaggaac gagttcaagt acttccaaag aatgaccaca    120
acctcttcag tggaaggtaa acagaatctg gtgattatgg gtaggaaaac ctggttctcc    180
attcctgaga gaatcgacc tttaaaggac agaattaata tagttctcag tagagaactc     240
aaagaaccac cacgaggagc tcattttctt gccaaaagtt tggatgatgc cttaagactt    300 attgacaac cggaattggc aagtaaagta gacatggttt ggatagtcgg aggcagttct     360
gtttaccagg aagccatgaa tcaaccaggc caccctcaga ctctttgtga caaggatcatg  420 caggaattg aaagtgacac gttttcccca gaaattgatt tggggaaata taaacttctc    480
ccagaatacc caggcgtcct ctctgaggtc caggaggaaa aaggcatcaa gtataagttt    540
gaagtctacg agaagaaaga ctaa                                            564

<210> SEQ ID NO 15
<211> LENGTH: 323
<212> TYPE: DNA
<213> ORGANISM: Artificial Sequence
<220> FEATURE:
<223> OTHER INFORMATION: SV40 Poly

<400> SEQUENCE: 15
caggaagatg cttcaagtt ctctgctccc ctcctaaagc tatgcatttt tataagacca      60
tgggactttt gctggcttta gatcataatc agccatacca catttgtaga ggttttactt    120
gctttaaaaa acctcccaca cctcccctg aacctgaaac ataaaatgaa tgcaattgtt     180
gttgttaact tgtttattgc agcttctaat ggttacaaat aaagcaatag catcacaaat    240
ttcacaaata aagcatttt ttcactgcat tctagttgtg gtttgtccaa actcatcaat    300
gtatcttatc atgtctggat cgg                                            323

METHODS FOR TREATMENT OF INFLAMMATORY DISEASE OR IL-6-MEDIATED CONDITION WITH GP130 PROTEIN

CROSS REFERENCE TO RELATED APPLICATIONS

This application is the National Stage of International Application No. PCT/IB132015/002459, filed Dec. 1, 2015 which claims the benefit of U.S. Provisional Application No. 62/086,054, filed Dec. 1, 2014, the contents of each of which are hereby incorporated herein by reference in their entirety.

SEQUENCE LISTING

In accordance with 37 CFR § 1.52(e)(5), a Sequence Listing in the form of a text file (entitled "P110641PC00_Sequence_listing.txt", created on May 31, 2017, and having a size of 39,640 bytes) is hereby incorporated by reference in its entirety.

BACKGROUND

IL-6 is a pleiotropic cytokine produced by hematopoietic and non-hematopoietic cells, e.g. in response to infection and tissue damage. IL-6 exerts its multiple biological activities through two main signalling pathways, a so-called classic ligand-receptor pathway via membrane-bound IL-6R present mainly on hepatocytes and certain leukocytes, and a trans-signalling pathway via circulating sIL-6R originating from proteolytic cleavage of the membrane-bound IL-6R or from alternative splicing.

In the classic pathway, IL-6 directly binds to membrane-bound IL-6R on the surface of a limited range of cell types. The IL-6/IL-6R complex associates with a pre-formed dimer of the signal-transducing gp130 receptor protein, causing steric changes in the gp130 homodimer and thereby initiating an intracellular signalling cascade. Classic signalling is responsible for acute inflammatory defence mechanisms and crucial physiological IL-6 functions, such as growth and regenerative signals for intestinal epithelial cells.

The extracellular domains of IL-6R and gp130 can be generated without the membrane-anchoring domains by translation of alternatively-spliced mRNAs resulting in sIL-6R and sgp130 variants. Additionally, the extracellular domain of IL-6R can be shed by membrane-bound proteases of the A disintegrin and metalloprotease (ADAM) family (in humans, ADAM17) to generate sIL-6R. In the trans-signalling process, sIL-6R binds to IL-6, forming an agonistic complex which binds to trans-membrane gp130 dimers present on a multitude of cell types that do not express membrane-bound IL-6R; IL-6 signalling by signal transducers and activators of transcription (STATs) is then induced in cells which do not normally respond to IL-6. The activity of the IL-6/sIL-6R complex is normally controlled by levels of sgp130 present in the circulation which effectively compete with membrane-bound gp130. Trans-signalling is mainly involved in chronic inflammation and has been shown to prevent disease-promoting mucosal T-cell populations from going into apoptosis.

It would be desirable to have a molecule that mimics the natural trans-signalling inhibitor sgp130, but with a higher binding affinity and, consequently, a stronger inhibitory activity. Moreover, it would be desirable to have a molecule that can be administered to humans with minimal toxicity and immunogenic potential.

SUMMARY OF THE INVENTION

It has now been found that a selective IL-6-trans-signalling inhibitor can be administered to humans without any significant deleterious effects over a large dosage range. Moreover, it has been surprisingly found that the terminal half-life of the inhibitor allows dosing on a weekly, biweekly (i.e., every other week), monthly or even lesser frequency.

In certain embodiments, the invention includes an inhibitor (e.g., a polypeptide dimer as disclosed herein) for the treatment of an inflammatory disease or IL-6-mediated condition, wherein the polypeptide is administered at a dose of 0.5 mg to 5 g. The invention also includes a method of treating inflammatory disease by administering the inhibitor (e.g., a polypeptide dimer as disclosed herein), where the inhibitor dose is from 0.5 mg to 5 g. The invention further includes use of such an inhibitor in the manufacture of a medicament for treating an inflammatory disease at the indicated dose. Preferably, a human is treated.

In other embodiments, the invention includes a polypeptide dimer as disclosed herein for treating an IL-6-mediated condition without significantly lowering neutrophil counts, platelet counts and/or levels of C-reactive protein or without lowering neutrophil counts, platelet counts and/or levels of C-reactive protein below a normal range in healthy subjects or patients suffering from an IL-6-mediated condition. The invention also includes a method of treating an IL-6-mediated condition by administering a polypeptide dimer as disclosed herein, wherein the method does not significantly lower neutrophil counts, platelet counts and/or levels of C-reactive protein. The invention further includes use of such a polypeptide dimer in the manufacture of a medicament for treating an IL-6-mediated condition without significantly lowering neutrophil counts, platelet counts and/or levels of C-reactive protein. Preferably, a human is treated.

BRIEF DESCRIPTION OF THE DRAWINGS

FIG. 7 shows the nucleotide (SEQ ID NO:8) and amino acid (SEQ ID NO: 9) sequence of the single gp130-Fc subunit.

FIGS. 8A-8F show nucleotide sequence elements of the expression plasmid pFER02. FIG. 8A depicts CMV IE Promoter (SEQ ID NO: 10). FIG. 8B depicts Human IgH PolyA (SEQ ID NO: 11). FIG. 8C depicts Amp (bla) gene (SEQ ID NO: 12). FIG. 8D depicts SV40 Promoter (SEQ ID NO: 13). FIG. 8E depicts Dihydrofolate Reductase Coding Sequence (SEQ ID NO: 14). FIG. 8F depicts SV40 Poly (SEQ ID NO: 15).

DETAILED DESCRIPTION OF THE INVENTION

Figure 2:
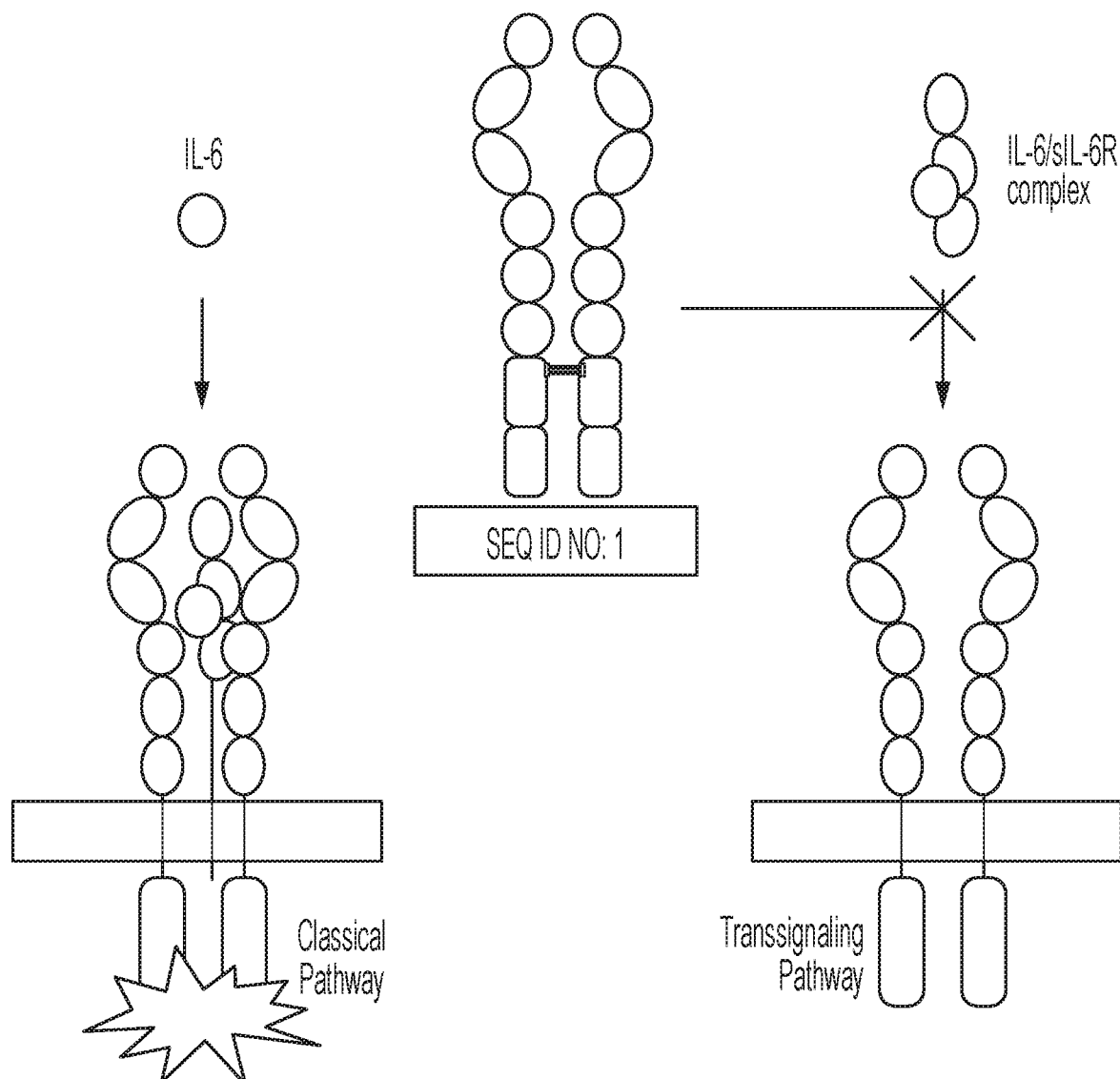
FIG. 2 shows that a polypeptide dimer comprising two monomers of SEQ ID NO: 1 does not interfere with IL-6 binding to membrane-bound IL-6R (classic signalling), but selectively binds to the IL-6/sIL-6R complex and prevents trans-signalling.

Preferred inhibitors of the invention include a dimer of two gp130-Fc fusion monomers (e.g., two monomers of SEQ ID NO:1). In its active form, the polypeptide of SEQ ID NO: 1 exists as a dimer linked by two disulfide linkages at Cys623 and Cys626 (FIG. 2). SEQ ID NO: 2 corresponds to the amino acid sequence of a gp130-Fc fusion monomer having the endogenous signal peptide. The signal peptide is removed during protein synthesis, resulting in the production of the polypeptide of SEQ ID NO: 1.

Figure 1:
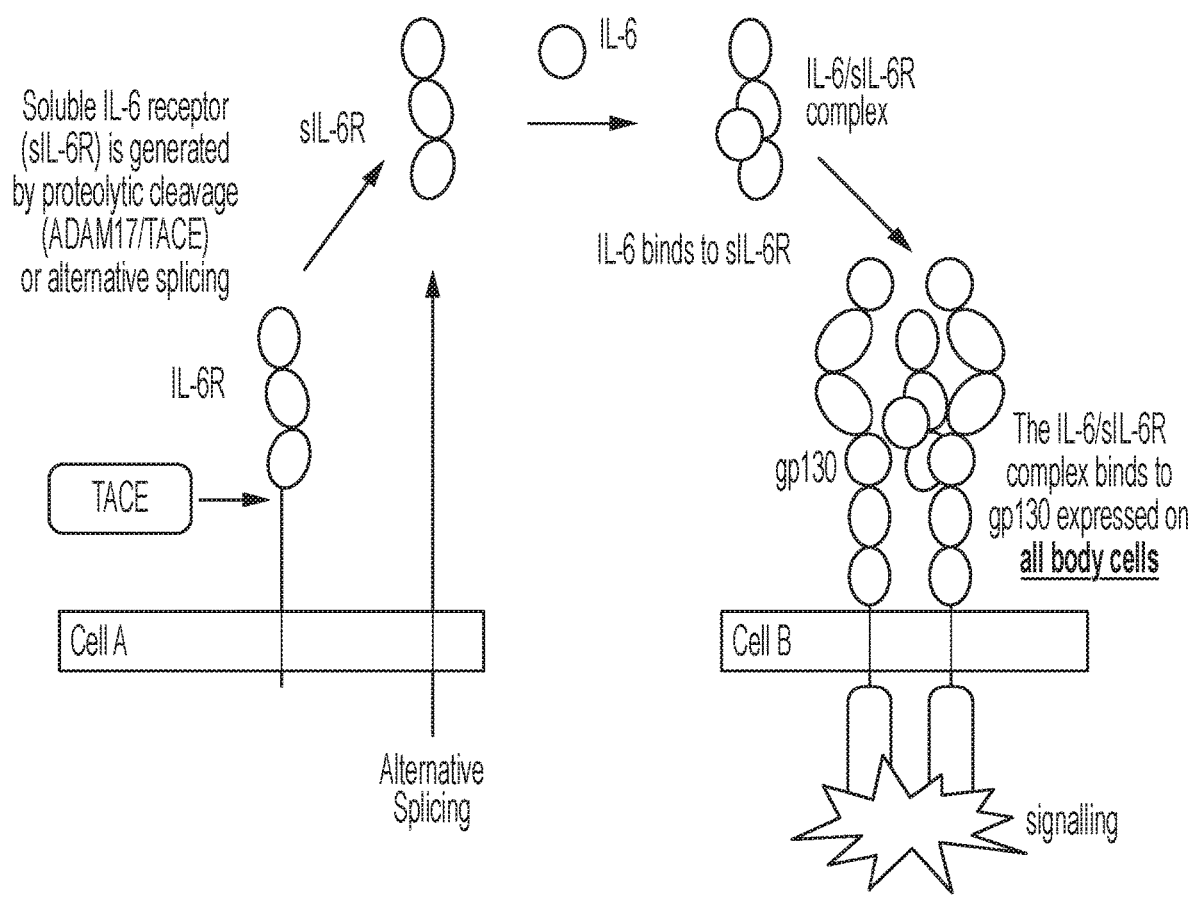
FIG. 1 shows the trans-signalling pathway of IL-6. sIL-6R generated from alternatively spliced mRNA or proteolytic cleavage is able to bind to IL-6 to form a IL-6/sIL-6 complex that binds to gp130 present on the vast majority of body cell types and induce a intracellular signalling cascade.

The polypeptide dimers described herein selectively inhibit excessive trans-signalling (FIG. 1) and induces apoptosis of the detrimental T-cells involved in multiple inflammatory diseases. The polypeptide dimer targets and neutralises IL-6/sIL-6R complexes and is therefore expected to only inhibit IL-6 trans-signalling in the desired therapeutic concentrations, leaving classic signalling and its many physiological functions, as well as its acute inflammatory defence mechanisms, intact (FIG. 2). The polypeptide dimer is believed to be unable to interfere with classic IL-6 signalling due to steric hindrance; the Fc portion is unable to insert into a cell membrane, making the gp130 portion unavailable for binding to membrane-bound IL-6/sIL-6R complex. Thus, the polypeptide dimer is expected to have efficacy similar to global IL-6 blockade (e.g., tocilizumab, sirukumab) but with fewer side effects.

Polypeptide dimers described herein preferably comprise gp130-Fc monomers having the sequence corresponding to SEQ ID NO:1. In certain embodiments, the monomers have the sequence corresponding to SEQ ID NO:2. In certain embodiments, polypeptide dimers described herein comprise polypeptides having at least 90%, 95%, 97%, 98%, 99% or 99.5% sequence identity to SEQ ID NO: 1 or SEQ ID NO:2. Preferably, the polypeptide comprises the gp130 D6 domain (in particular amino acids TFTTPKFAQGE: amino acid positions 585-595 of SEQ ID NO:1), AEGA in the Fc domain hinge region (amino acid positions 609-612 of SEQ ID NO:1) and does not comprise a linker between the gp130 portion and the Fc domain. In a preferred embodiment, the disclosure provides a polypeptide dimer comprising two monomers having an amino acid sequence at least 90% sequence identify to SEQ ID NO: 1, wherein the amino acid sequence comprises the gp130 D6 domain, AEGA in the Fc domain hinge region, and there is no linker present between the gp130 portion and the Fc domain. In a preferred embodiment, the disclosure provides a polypeptide dimer comprising two monomers having an amino acid sequence at least 90% sequence identify to SEQ ID NO: 2, wherein the amino acid sequence comprises the gp130 D6 domain, AEGA in the Fc domain hinge region, and there is no linker present between the gp130 portion and the Fc domain.

It is desirable for polypeptides to be substantially free of galactose-alpha-1,3-galactose moieties, as these are associated with an immunogenic response. It was surprisingly found that dimers of the invention have low levels of such moieties. In preferred embodiments, the polypeptide dimer contains no greater than 6% of galactose-alpha-1,3-galactose per mole polypeptide. Preferably, the polypeptide dimer contains no greater than 4 mole %, 3 mole %, 2 mole %, 1 mole %, 0.5 mole %, 0.2 mole %, 0.1 mole % or even an undetectable level of galactose-alpha-1,3-galactose (e.g., as measured by WAX-HPLC, NP-HPLC or WAX, preferably as determined by WAX-HPLC). In other embodiments, the polypeptide dimer contains less than 6%, 4%, 3%, 2%, 1%, 0.5%, 0.2%, or even 0.1% of galactose-alpha-1,3-galactose, relative to the total amount of glycans, either by mass or on a molar basis.

It is also desirable for a polypeptide of the invention to be sialylated. This has the advantage of increasing the half-life of polypeptides of the invention. Each chain of the polypeptide dimer contains 10 N-glycosylation sites; nine N-glycosylation sites are located in the gp130 portion and one N-glycosylation site is located in the Fc portion. The polypeptide therefore contains a total of 20 glycosylation sites. In certain embodiments, a mean of at least 52% or at least 54% of glycans on the polypeptide include a sialic acid residue, such as a mean from 52-65% (e.g., as measured by WAX-HPLC, NP-HPLC or WAX, preferably as determined by WAX-HPLC). Preferably, the polypeptide of the invention has an approximate molecular weight of 220 kDa; each 93 kDA having an additional ~20 kDa molecular weight derived from 10 N-glycosylation chains.

It is further desirable to minimize the extent to which polypeptides aggregate, which is herein referred to as oligomerization which results in oligomeric aggregates. "Oligomeric aggregates" as used herein, does not refer to the active dimerized peptide. Instead, the term refers to at least a dimer of active dimers. In was surprisingly found that the peptide dimers of the invention display low levels of aggregation. In certain embodiments, less than 5%, less than 4%, less than 3%, less than 2%, less than 1.5%, or even less than 1.0% of the polypeptide is present as an oligomer. The oligomer content can be measured, for example, by size exclusion chromatography-multi angle light scatting (SEC-MALS) or SEC-UV.

Preferably, the polypeptide dimer is present in its full-length form (e.g., includes two full length monomers, e.g., of SEQ ID NO:1). However, cell culture can produce a truncated variant referred to herein as the single gp130 form (SGF). SGF is a covalently-bound two-chain molecule, one chain comprising a full-length gp130-Fc monomer (e.g., of SEQ ID NO:1) and a second chain comprising a truncated gp130-Fc monomer (e.g., a truncation of SEQ ID NO:1), which second chain includes the Fc domain and lacks most or all of the gp130 domain (e.g., terminated before the linker sequence to the Fc region). Studies to date demonstrate that SGF does not have a heterogeneous amino-terminus. SGF can be formed at consistent levels in a bioreactor and once formed, SGF levels are not readily changed during purification, processing or accelerated storage conditions. SGF levels can be difficult to remove during purification due to similar physical-chemical properties to the full-length form of the polypeptide dimer; thus efforts to remove SGF can result in a significant reduction in yield. It was surprisingly found that polypeptide dimers of the invention are nearly always full-length. In certain embodiments, the composition of the invention comprises polypeptide dimers comprising no greater than 4.0% by weight, 3.0% by weight, 2.0% by weight or even 1.5% by weight of polypeptides that are a truncated variation of the polypeptide of SEQ ID NO: 1 with respect to polypeptides of SEQ ID NO: 1. In certain embodiments, the composition of the invention comprises no greater than 4.0% by weight, 3.0% by weight, 2.0% by weight or even 1.5% by weight of polypeptides that are a truncated variation of the polypeptide of SEQ ID NO: 2 with respect to polypeptides of SEQ ID NO: 2.

Dosing

The doses described herein represent a dose range that are believed to be safe and tolerable, based upon Phase I data. Other compounds targeting IL-6R or IL-6 have often displayed, in early clinical trials, decreased neutrophil and platelet counts and lower levels of C-reactive protein (CRP) both in healthy subjects and patients with RA. However, the observed levels in neutrophil and platelet counts in healthy subjects dosed with the polypeptide of the invention were still within the normal range. It appears, from the results from the Phase I program, that the polypeptide of the invention does not display the same effects on biomarkers as compounds targeting IL-6R or IL-6.

In the two trials with the polypeptide dimers comprising monomers of SEQ ID NO: 1, an ex vivo assay measuring the level of activation of STAT 3 by stimulating whole blood samples from the subjects with hyper IL-6 was employed as an assessment of the activity of the drug. Concentration levels of the polypeptide comprising monomers of SEQ ID NO: 1 above 1 µg/mL are believed to be related to suppressed signal to baseline in the secondary messenger (STAT3) assay. The concentration level of the polypeptide dimers comprising monomers of SEQ ID NO: 1 would correspond to the peak levels of the 7.5 mg dose. A dose of 75 mg administered as an i.v. infusion has been shown to have a concentration above 1 µg/mL at steady state for a dosing interval of one week. The corresponding dose administered every two weeks is 300 mg. It is believed that 60 mg administered as a subcutaneous injection is believed to result in the same steady state for dosing every week.

In certain embodiments, the dose is from 0.5 mg to 5 g polypeptide dimer. For example, the dose can be from 5 mg to 3 g, 10 mg to 2 g, 60 mg to 1 g or preferably from 60 mg to 750 mg.

The polypeptide dimers can be administered at a frequency appropriate for the intended condition. In certain embodiments, the polypeptide dimer is dosed once every 7-60 days. For example, the polypeptide dimers can be dosed once every 7-30 days or 7-20 days. In preferred embodiments, the dose occurs weekly (once every 7 days) or biweekly (once every 14 days). Doses can also occur on a daily basis or twice- or thrice-weekly. A dose refers to a single dosing episode, whether the dose is a unit dosage form or multiple unit dosage forms taken together (e.g., ingestion of two or more pills, receiving two or more injections). As discussed below, this dose frequency could not be predicted from animal studies. Human clinical trials found a mean half-life of 4.6 days to 5.5 days. In contrast, cynomolgus monkeys had a half-life of only 0.7 days when administered the polypeptide dimers intravenously and 1.4-1.5 days subcutaneously.

The polypeptide dimer of the invention is typically administered parenterally, such as intravenously or subcutaneously. Administration can occur according to one of the dosing frequencies disclosed herein.

In certain embodiments, the polypeptide dimer is administered intravenously, dosed once every 7-60 days with a dose from 60 mg to 1 g.

In certain such embodiments, the polypeptide dimer is administered intravenously, dosed once every 7-30 days with a dose from 60 mg to 1 g.

In an exemplary embodiment, the polypeptide dimer is administered intravenously, dosed weekly with a dose from 60 mg to 1 g.

In another exemplary embodiment, the polypeptide dimer is administered intravenously, dosed biweekly with a dose from 60 mg to 1 g.

In certain embodiments, the polypeptide dimer is administered subcutaneously, dosed once every 7-60 days with a dose from 60 mg to 600 g.

In certain embodiments, the polypeptide dimer is administered subcutaneously, dosed once every 7-30 days with a dose from 60 mg to 600 g.

In an exemplary embodiment, the polypeptide dimer is administered subcutaneously, dosed once weekly with a dose from 60 mg to 600 g.

In another exemplary embodiment, the polypeptide dimer is administered subcutaneously, dosed once biweekly with a dose from 60 mg to 600 g.

Safety

The polypeptide dimer comprising monomers of SEQ ID NO: 1 has been administered up to 750 mg as a single dose and 600 mg once weekly for 4 weeks. The safety profile of the polypeptide was favourable with few adverse events occurring in all treatment groups, including the placebo group, all being mild or moderate. No apparent dose-related trends in incidence or frequency of adverse events were observed. There were no apparent dose-related trends or treatment related changes in vital signs, ECG, or clinical chemistry parameters. Three events of infusion reactions occurred, all were mild/moderate with cutaneous symptoms like urticaria and swelling, and rapidly resolved without any sequelae.

Overall, the polypeptide dimer comprising monomers of SEQ ID NO: 1 was safe and well tolerated when administered i.v. up to 600 mg once weekly for 4 weeks and up to 750 mg as a single dose.

The potential risk of the polypeptide comprising monomers of SEQ ID NO: 1 in humans can also be addressed indirectly by analysing the clinical studies investigating similar compounds targeting IL-6R or IL-6. To date, there is no approved compound which blocks the same signalling pathway as this polypeptide dimer, i.e. targeting and neutralising IL-6/sIL-6R-complex to inhibit the trans-signalling pathway, without any interaction with either IL-6 or IL-6R individually. However, there are experiences with compounds targeting IL-6 receptors. One of these compound is tocilizumab, which has been approved in Europe and United States. Tocilizumab binds specifically to both soluble and membrane-bound IL-6 receptors and has been shown to inhibit sIL-6R and mIL-6R mediated signalling.

The most common reported adverse drug reactions in RA patients treated with tocilizumab (occurring in ≥5%) were upper respiratory tract infections, nasopharyngitis, headache, hypertension and increased ALT. The most serious adverse drug reactions were serious infections, complications of diverticulitis and hypersensitivity reactions. Decreases in neutrophil and platelet counts have occurred following treatment with tocilizumab. Decreases in neutrophil counts below $10^9$/L occurred in 3.4% of patients on tocilizumab 8 mg/kg plus disease-modifying anti-rheumatic drugs (DMARDs). Approximately half of the patients who developed an ANC <$10^9$/L did so within 8 weeks after starting therapy. Decreases below $5\times10^8$/L were reported in 0.3% patients receiving tocilizumab 8 mg/kg and DMARDs. Severe neutropenia may be associated with an increased risk of serious infections, although there has been no clear association between decreases in neutrophils and the occurrence of serious infections in clinical trials with tocilizumab to date. Events reported during the infusion were primarily episodes of hypertension; events reported within 24 hours of finishing an infusion were headache and skin reactions (rash, urticaria). These events were not treatment limiting. Clinically significant hypersensitivity reactions associated with tocilizumab and requiring treatment discontinuation were reported in a total of 13 out of 3,778 patients (0.3%) treated with tocilizumab during the controlled and open-label clinical studies. These reactions were generally observed during the second to fifth infusions of tocilizumab. Gastrointestinal perforations, primarily in patients with a history of diverticulitis, have been reported as rare events, both in tocilizumab clinical trials and post-marketing. The etiology is unclear but RA patients have a generally increased risk for perforations of both the upper and lower GI tract (regardless of DMARD therapy); the risk is highest in RA patients on glucocorticoid therapy, NSAIDs, or with a history of diverticulitis. Fatal anaphylaxis has been reported after marketing authorisation during treatment with tocilizumab. It should be noted that RA patients may have other background diseases as confounding factors.

Because the polypeptide dimer comprising monomers of SEQ ID NO: 1 is a first-in-class fusion protein, comparisons with the different monoclonal antibody products with different mechanisms of action is of limited value. In contrast to other products which completely block IL-6 activity, this polypeptide dimer is believed to only interfere with the IL-6/sIL-6R complex, leaving the membrane bound IL-6 pathway accessible.

IL-6 has a broad involvement in the immune and inflammatory responses in the body. When both soluble and membrane-bound IL-6R is blocked, there is potentially an increased risk of infections and other immuno-dependent diseases as well as a less prominent inflammatory response. While not wishing to be bound by theory, it is believed that treatment with the polypeptide dimer comprising monomers of SEQ ID NO: 1, which only targets the IL-6/sIL-6R complex, would prevent the perpetuation of chronic intestinal inflammation in IBD and preserve the acute phase inflammatory response activated by classical IL-6 signalling, thereby lowering the risk of opportunistic infections. However, it could not be predicted whether there is a concentration of polypeptide dimer of the invention above which classical IL-6 signalling would be impacted. Thus, the data herein surprisingly demonstrate that there is less impact on classical IL-6 signalling relative to other treatments targeting IL-6 activity.

Based on the data presented herein, an advantage of the polypeptide dimer of the invention is that it may have a lesser effect on neutrophil counts, platelet counts and/or levels of C-reactive protein than other compounds that inhibit IL-6. In certain embodiments, the polypeptide dimer of the invention does not significantly lower neutrophil counts, platelet counts and/or levels of C-reactive protein or without lowering neutrophil counts, platelet counts and/or levels of C-reactive protein below a normal range in healthy subjects or patients suffering from an IL-6-mediated condition. For example, the administration of the polypeptide dimer at a dose amount described herein maintains neutrophil counts, platelet counts and/or levels of C-reactive protein within a normal physiological range. In certain embodiments, neutrophil counts, platelet counts and/or levels of C-reactive protein are no more than 50%, 40%, 30%, 20%, 15%, 10% or 5% less than the lower limit of the normal physiological range. The measurement of neutrophil counts, platelet counts and/or levels of C-reactive protein can occur immediately after treatment, one day after days, three days after treatment, one week after treatment, two weeks after treatment, one month after treatment, three months after treatment, six months after treatment or a year after treatment.

The determination of neutrophil counts, platelet counts, and levels of C-reactive protein can be performed by any number of assays well-known in the art. Neutrophil count, also referred to as absolute neutrophil count (ANC) is a measure of the number of neutrophil granulocytes present in blood (see, e.g., Al-Gwaiz L A, Babay H H (2007). "The diagnostic value of absolute neutrophil count, band count and morphologic changes of neutrophils in predicting bacterial infections". Med Princ Pract 16 (5): 344-7). Normal physiological values for C-reactive protein in adult males and females are 0-5.00 mg/L (e.g., via turbidimetry). Normal physiological values for neutrophils in adult females are $1.61$-$6.45 \times 10^9$ per L (absolute value, e.g., via laser flow cytometry) or 37.9-70.5% (calculated); in adult males, the corresponding values are $1.46$-$5.85 \times 10^9$ per L and 38.2-71.5%. Normal physiological values for platelets in adult females are $173$-$369 \times 10^9$ per L (e.g., via high frequency impedance measurement); in adult males, the corresponding values are $155$-$342 \times 10^9$ per L.

The polypeptide dimer of the invention preferably does not significantly induce the formation of antibodies (e.g., antibodies to the polypeptide dimer) in humans. Even more preferably, the antibodies are not neutralizing antibodies. In certain embodiments, antibodies against the polypeptide dimer of the invention are detectable in fewer than 5%, 2%, 1%, 0.5%, 0.2%, 0.1% or 0.01% of treated subjects or patients. Typically, the limit of detection is approximately 9 ng/mL serum.

Indications

In acute inflammation, IL-6 has been shown to induce the acute phase response in the liver leading to release of the cascade of acute phase proteins, in particular CRP. By forming a complex with sIL-6R shed by apoptotic neutrophils at the site of inflammation and binding of the resulting IL-6/sIL-6R trans-signalling complex to the signal transducer gp130 on endothelial cells, IL-6 induces expression of chemokines such as monocyte chemotactic protein (MCP)-1 and attracts mononuclear cells. This leads to the resolution of acute inflammation and to the initiation of an adaptive immune response. Thus, in acute inflammation, IL-6 with sIL-6R complex supports the transition between the early predominantly neutrophilic stage of inflammation and the more sustained mononuclear cell influx ultimately also leading to the resolution of inflammation.

Chronic inflammation, such as in Crohn's disease (CD), ulcerative colitis (UC), rheumatoid arthritis (RA) or psoriasis, is histologically associated with the presence of mononuclear cells, such as macrophages and lymphocytes, persisting in the tissue after having been acquired for the resolution of the acute inflammatory phase. In models of chronic inflammatory diseases, IL-6 seems to have a detrimental role favouring mononuclear-cell accumulation at the site of injury, through induction of continuous MCP-1 secretion, angio-proliferation and anti-apoptotic functions on T-cells.

Inflammatory bowel disease (IBD), namely CD or UC, is a chronic inflammation occurring in the gut of susceptible individuals that is believed to be independent of a specific pathogen. Alterations in the epithelial mucosal barrier with increased intestinal permeability lead to an enhanced exposure of the mucosal immune system to luminal antigens, which causes an inappropriate activation of the intestinal immune system in patients. The uncontrolled activation of mucosal CD4+ T-lymphocytes with the consecutive excessive release of proinflammatory cytokines induces pathogenic gastrointestinal inflammation and tissue damage. There is a consensus that the main activated immune cells involved in the pathogenesis of IBD are intestinal T-cells and macrophages.

IL-6 is shown to be a central cytokine in IBD in humans. Patients with CD and UC have been found to produce increased levels of IL-6 when compared with controls, the IL-6 levels being correlated to clinical activity. CD patients have also been found to have increased levels of sIL-6R and consequently, IL-6/sIL-6R complex in serum. Lamina propria mononuclear cells obtained from surgical colon specimens from patients with CD and UC showed that both CD4+ T-cells and macrophages produced increased amounts of IL-6 compared to controls. sIL-6R was found to be released via shedding from the surface of macrophages and mononuclear cells with increased production associated with elevated levels of IL-6. In patients with CD, mucosal T-cells showed strong evidence for IL-6 trans-signalling with activation of STAT3, bcl-2 and bcl-x1. The blockade of IL-6 trans-signalling caused T-cell apoptosis, indicating that the IL-6/sIL-6R system mediates the resistance of T-cells to apoptosis in CD.

Thus, in IBD patients, acquired accumulation of disease-promoting CD4+ T-cells in the lamina propria leading to perpetuation of inflammation is critically dependent on anti-apoptotic IL-6/sIL-6R trans-signalling. It is believed that by acting on the IL-6/sIL-6R complex, the polypeptide dimer disclosed herein is useful in treating CD and other inflammatory diseases.

Thus, the polypeptide dimer of the invention can treat IL-6-mediated conditions. IL-6-mediated conditions include inflammatory disease or a cancer. In this regard, the polypeptides and compositions described herein may be administered to a subject having an inflammatory disease, such as juvenile idiopathic arthritis, Crohn's disease, colitis (e.g., colitis not associated with IBD, including radiation colitis, diverticular colitis, ischemic colitis, infectious colitis, celiac disease, autoimmune colitis, or colitis resulting from allergies affecting the colon), dermatitis, psoriasis, uveitis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of, diabetes, gout, cryopyrin-associated periodic syndrome, and chronic obstructive pulmonary disorder.

Preferably, the inflammatory disease or IL-6-mediated condition is inflammatory bowel disease, preferably wherein the treatment induces the remission of inflammatory bowel disease. Preferably, the inflammatory bowel disease is Crohn's disease or ulcerative colitis, preferably wherein the treatment maintains the remission of inflammatory bowel disease. Preferably, the inflammatory disease or IL-6-mediated condition is rheumatoid arthritis, psoriasis, uveitis or atherosclerosis. Preferably, the inflammatory disease or IL-6-mediated condition is colitis not associated with inflammatory bowel disease, preferably wherein the colitis is radiation colitis, diverticular colitis, ischemic colitis, infectious colitis, celiac disease, autoimmune colitis, or colitis resulting from allergies affecting the colon.

For inflammatory disease such as inflammatory bowel disease, treatment can include remission of the condition, maintenance of remission of the condition, or both.

Other embodiments provide a method of treating, reducing the severity of or preventing a cancer, including, but not limited to multiple myeloma, plasma cell leukemia, renal cell carcinoma, Kaposi's sarcoma, colorectal cancer, gastric cancer, melanoma, leukemia, lymphoma, glioma, glioblastoma multiforme, lung cancer (including but not limited to non-small cell lung cancer (NSCLC; both adenocarcinoma and squamous cell carcinoma)), non-Hodgkin's lymphoma, Hodgkin's disease, plasmocytoma, sarcoma, thymoma, breast cancer, prostate cancer, hepatocellular carcinoma, bladder cancer, uterine cancer, pancreatic cancer, esophageal cancer, brain cancer, head and neck cancers, ovarian cancer, cervical cancer, testicular cancer, stomach cancer, esophageal cancer, hepatoma, acute lymphoblastic leukemia (ALL), T-ALL, acute myelogenous leukemia (AML), chronic myelogenous leukemia (CML), and chronic lymphocytic leukemia (CLL), salivary carcinomas, or other cancers.

Further embodiments of the present disclosure provide a method of treating, reducing the severity of or preventing a disease selected from the group consisting of sepsis, bone resorption (osteoporosis), cachexia, cancer-related fatigue, psoriasis, systemic-onset juvenile idiopathic arthritis, systemic lupus erythematosus (SLE), mesangial proliferative glomerulonephritis, hyper gammaglobulinemia, Castleman's disease, IgM gammopathy, cardiac myxoma and autoimmune insulin-dependent diabetes.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The polypeptide dimer of the invention can be administered in conjunction with a second active agent. The second active agent can be one or more of 5-aminosalicylic acid, azathioprine, 5-mercaptopurine and a corticosteroid. Dosage regimes for the administration of 5-aminosalicylic acid, azathioprine, 5-mercaptopurine and corticosteroids are well-known to a skilled person.

The polypeptide dimers may be produced, for example, by expressing the monomers, e.g. monomers comprising SEQ ID NO: 1, in cells. In an exemplary embodiment, a vector comprising a nucleic acid encoding SEQ ID NO: 1 or SEQ ID NO:2 is transfected into cells. The design of the expression vector, including the selection of regulatory sequences, may depend on such factors as the choice of the host cell to be transformed, the level of expression of protein desired, and so forth. Regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. The host cell may be a mammalian, insect, plant, bacterial, or yeast cell, preferably the cell is a mammalian cell such as a CHO cell.

The transfected cells are cultured to allow the cells to express the desired protein. The cells and culture media are then collected and polypeptide dimers are purified, e.g., by chromatography column steps (e.g., MAbSelect Sure, SP Sepharose, Capto Q). The dimer can also be concentrated and/or treated with viral reduction/inactivation steps. The resulting dimers can then be used to prepare compositions, preferably pharmaceutical compositions useful for therapy.

EXEMPLIFICATION

Example 1

Animal Studies

Example 1a

Mouse Pharmacokinetics

Four groups with 54 mice (27 male and 27 female) weighing 25-38 g received a single dose of the polypeptide of SEQ ID NO: 1 in its active dimerized form ("Peptide 1") by either i.v. (3 mg/animal) or s.c. (0.3, 3 and 30 mg/animal) injection.

Bioavailability was approximately 60%, and apparent dose linearity was observed for AUC, $AUC_t$ and $C_{max}$. The $t_{max}$ of 8-24 hours was as expected for a protein. Peptide 1 was cleared slowly from the systemic circulation with a clearance of 142 mL/day/kg. Distribution volumes estimated by the elimination phase (Vz) and first moment curve (Vss) were 397 mL/kg and 284 mL/kg, respectively, indicating that Peptide 1 was distributed outside the vascular bed. The terminal half-life ranged from 1.3-2.3 days.

Example 1b

Rat Pharmacokinetics

Single-Dose Administration

The single-dose PK of Peptide 1 was investigated after i.v. and s.c. administration in two different strains of rats, Sprague Dawley (8 rats/group) and Wistar (24 rats/group), showing somewhat different results. The clearance (57 and 93 mL/kg/day, respectively) and distribution volume appeared to be lower in the Sprague Dawley rat, with a 2-fold higher bioavailability, 60%, as compared to approximately 30% for the Wistar rat. $T_{max}$ was observed 0.5-1.5 days after s.c. administration, and the terminal half-life was approximately 2 days, ranging from 1.7-2.7 days, with only small differences between the two administration routes.

Repeat-Dose Administration

Intravenous Administration

Rats (n=18) received i.v. bolus doses 10, 30 and 100 mg/kg/occasion twice a week for 2 weeks. The increase in $C_{max}$ and AUC after the first administration seemed to be approximately dose linear. However, exposure appeared to be consistently higher in males than in females at all dose levels. The 100 mg/kg/occasion group reached $C_{max}$ levels of 2100 µg/mL for male rats and 1740 µg/mL for female rats. The AUCt values were 942 and 642 day×µg/mL.

After two weeks, the systemic exposure to Peptide 1 in rats decreased for the 10 mg/kg and 30 mg/kg dose groups. As anti-drug antibody (ADA) responses were confirmed in all animals by Week 8 of the study, decreases in expected exposure over time may be attributed to ADA-mediated clearance of Peptide 1.

Subcutaneous Administration

In 2- and 4-week repeat dose s.c. studies, the $C_{max}$ and AUC after the first administration seemed to increase approximately dose linearly. However, at the last dose, a notably lower drug exposure was seen, possibly due to antibody formation; all animals tested showed antibodies towards Peptide 1.

Example 1c

Cynomolgus Monkey Pharmacokinetics

Single-Dose Administration

The PK of single administration of Peptide 1 was investigated in male and female cynomolgus monkeys at doses of 0.1-100 mg/kg s.c. (n=4) and 1.0 mg/kg i.v (n=4). The bioavailability was approximately 60% following s.c. administration with a $t_{max}$ of 6-24 hours. The clearance was 98 mL/day/kg, and the distribution volume approximately 70-90 mL/kg. The half-life determined after i.v. administration was 0.68 days, and approximately 1.5 days after s.c. administration.

Repeat-Dose Administration

Cynomolgus monkeys were dosed s.c. with 2 (n=4), 10 (n=4), 50 (n=2), or 100 (n=2) mg/kg Peptide 1 twice weekly for 2 weeks, and with 10 (n=4), 30 (n=4), or 100 (n=4) mg/kg Peptide 1 twice weekly for 4 weeks. The exposure by means of $C_{max}$ and AUC increased approximately dose linearly, and similar exposure and maximal concentration between the first and last dose at the higher doses were observed after 2 weeks. However, after 4 weeks, the last administered dose showed a lower drug exposure compared to the first administration, possibly due to antibody formation. The mean half-life of Peptide 1 ranged from 1.0-1.8 days for the first administration in the different treatment groups with a shorter half-life after the last administration.

Example 2

Clinical Trial 000067 (Single Dose)

Design

This was a single-dose, placebo controlled, single blinded, randomised within dose, parallel group dose-escalating trial. The trial was conducted in two parts, where Part 1 included healthy subjects and Part 2 included patients with CD in clinical remission. The objective was to examine the safety and tolerability, and if possible, to obtain signs of pharmacological effects, after single doses of Peptide 1.

In Part 1, 64 subjects were included, of whom 48 (44 men, 4 women) received active treatment and 16 (all men) received placebo. Seven doses were investigated and administered as an i.v. infusion over 30 minutes (0.75 mg, 7.5 mg, 75 mg), or 1 hour (150 mg, 300 mg, 600 mg, and 750 mg). In addition, 6 subjects received a s.c. dose of 60 mg Peptide 1 and 2 subjects received a s.c. dose of placebo. Peptide 1 was administered at 15 mg/mL in 25 mM histidine, 200 mM sucrose and 0.1 mg/mL polysorbate 20.

In Part 2, 24 patients were included, of whom 18 (11 men, 7 women), received active treatment (75 mg, 300 mg, and 750 mg) and 6 (4 men, 2 women) received placebo, all administered by i.v.

Results

Figure 3:
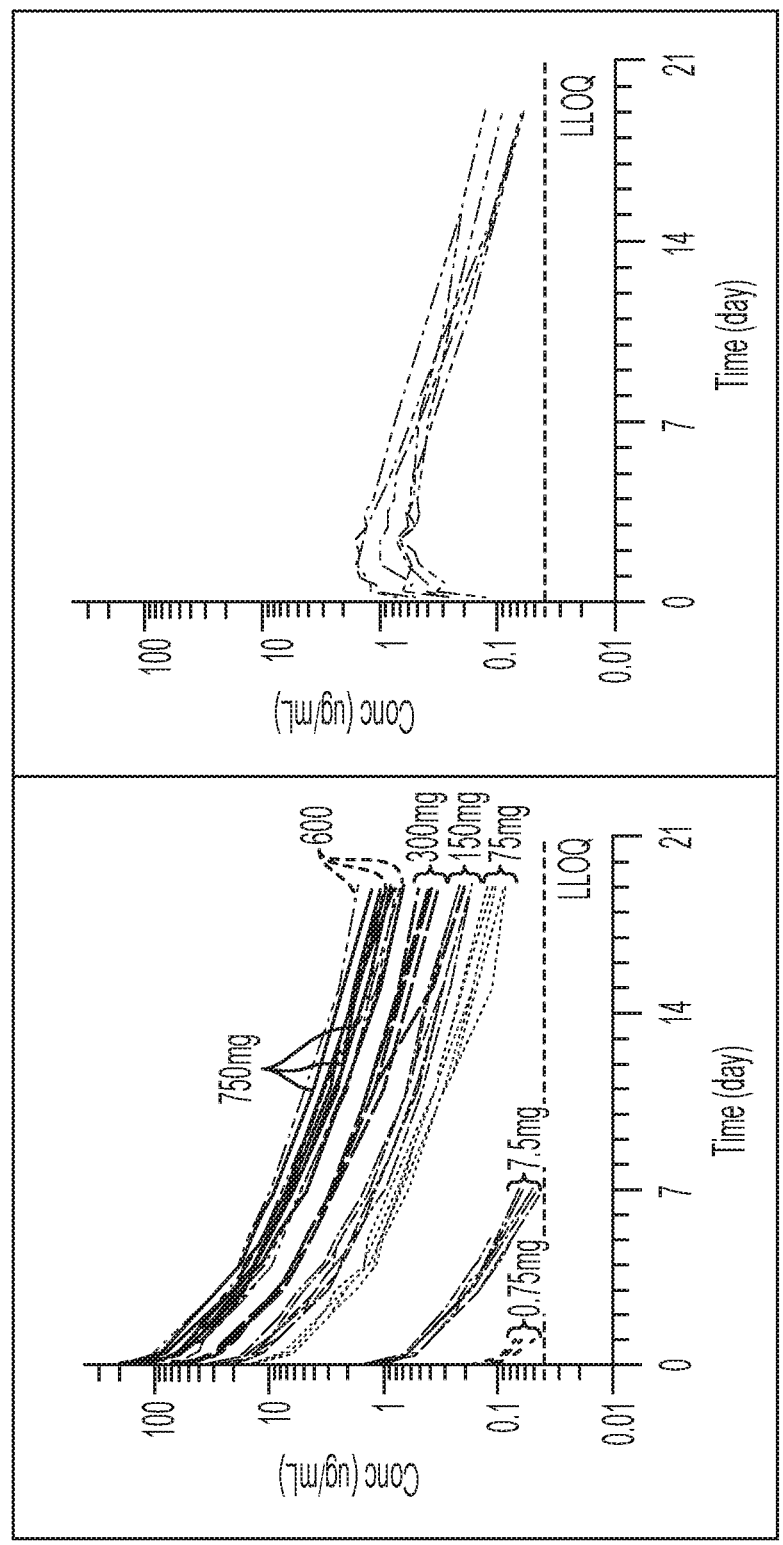
FIG. 3 shows profiles after i.v. infusion of Peptide 1 (left panel) at 0.75 mg, 7.5 mg, 75 mg, 150 mg, 300 mg, 600 mg and 750 mg and s.c. injection (right panel) at 60 mg (2×2 mL).

The PK evaluation after i.v. administrations of Peptide 1 showed dose proportionality for both AUC and Cmax in the range 0.75 mg to 750 mg, the Cmax concentrations in plasma ranging from 0.2 to 170 µg/mL (FIG. 3). The clearance was approx. 0.13 L/h, the mean terminal half-life approx. 4.5 days, and the distribution volume approx. 20 L, the latter indicating some extravascular distribution. The s.c. administration of 60 mg Peptide 1 showed a Cmax of 1.1 µg/mL at 2.3 days, and a half-life of 5.0 days. The bioavailability after s.c. administration of Peptide 1 was calculated to be approx. 50%. There was no indication of target-mediated drug disposition.

Figure 4:
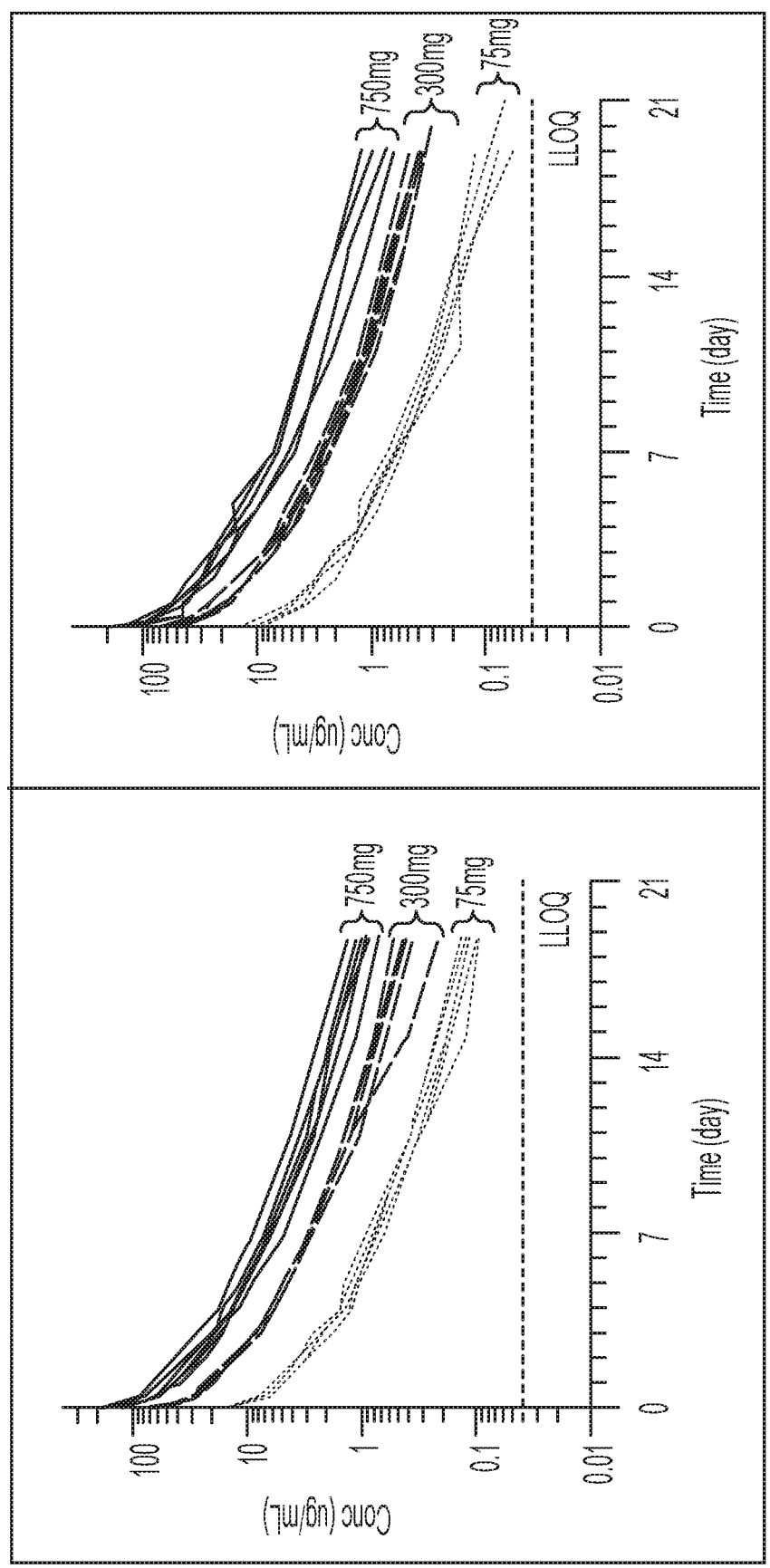
FIG. 4 shows profiles after intravenous administration at 75 mg, 300 mg and 750 mg in healthy subjects (left panel) and CD patients in clinical remission (right panel).

The i.v. administration of 75, 300, and 750 mg to CD patients in remission showed very similar results as for the healthy subjects (FIG. 4). The AUC and Cmax were dose proportional with Cmax concentrations of 16, 76, and 186 µg/mL (16, 77, and 161 µg/mL for healthy subjects). The clearance was approx. 0.13 L/h, the mean terminal half-life approx. 4.6 days, and the distribution volume approx. 22 L.

The safety profile of Peptide 1 was favourable with few adverse events occurring in all treatment groups, including the placebo group, all being mild or moderate. No apparent dose-related trends in incidence or frequency of adverse events were observed. The infusions were discontinued in two subjects, one due to mild (Part 1, 300 mg group) and one due to moderate (Part 2, 75 mg group) infusion reactions.

There were no apparent dose-related trends or treatment-related changes in vital signs, ECG, or clinical chemistry parameters (including neutrophil counts, platelet counts, or C-reactive protein levels).

One healthy subject in the 300 mg group showed non-neutralising treatment emergent anti-Peptide 1 antibodies at the follow-up visit 5-6 weeks after administration.

Overall, Peptide 1 was safe and well tolerated when administered intravenously up to 750 mg as a single i.v. dose, and at 60 mg as a single s.c. dose.

Example 3

Clinical Trial 000115 (Multiple Ascending Dose)

Design

This was a placebo controlled, double-blind, within dose-group randomised, parallel group trial with the objective to investigate the safety, tolerability, and pharmacokinetics of multiple ascending doses of Peptide 1. The doses investigated were 75, 300 and 600 mg Peptide 1 administered once a week, for 4 weeks, by i.v. infusion over 30 minutes (75 mg) or 1 hour (300 mg and 600 mg).

Twenty-four (24) healthy subjects were included, of whom 18 (11 men and 7 women) received active treatment and 6 (2 men and 4 women) received placebo.

Results

Figure 5:
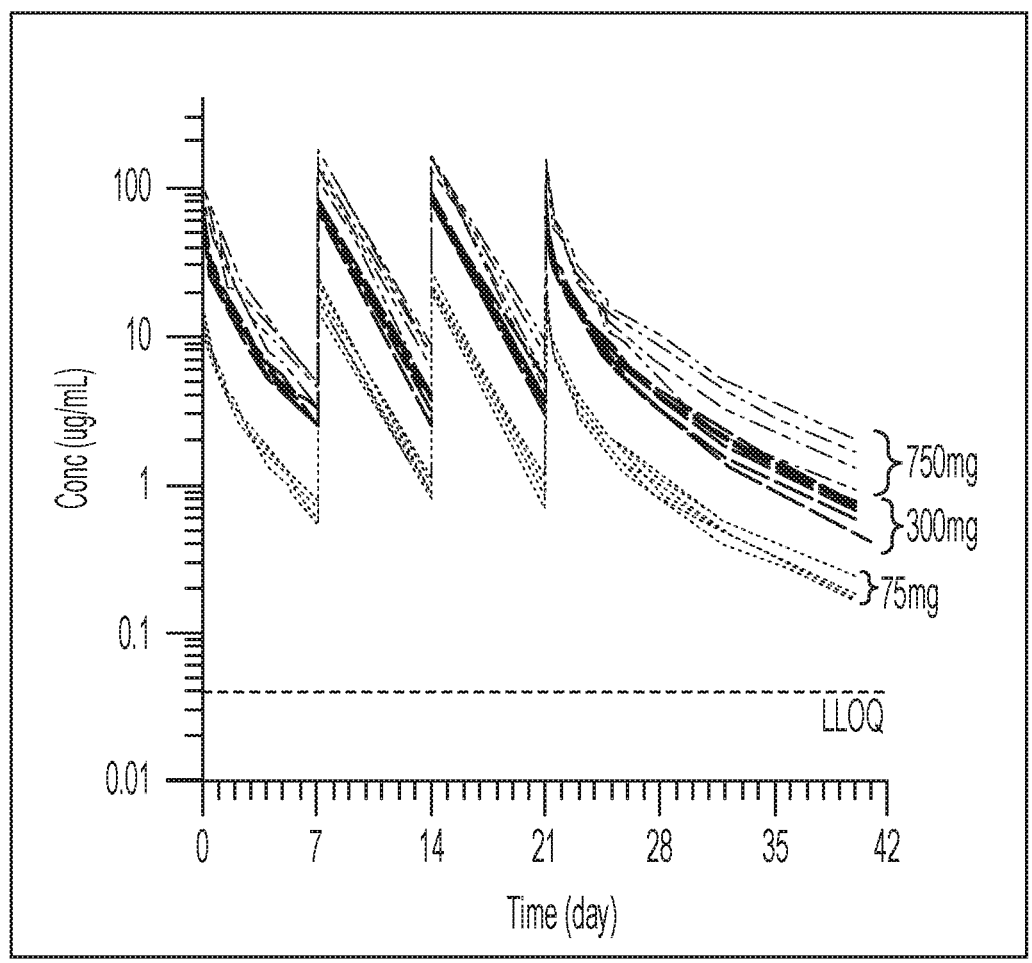
FIG. 5 shows profiles after intravenous administration at 75 mg, 300 mg and 750 mg once a week for 4 weeks in healthy subjects.

The PK evaluation showed very close characteristics on the first and last treatment days, and similar to the results in the single-dose study. The AUC and Cmax were dose proportional after first and fourth dosing with Cmax concentrations of 19, 78, and 148 µg/mL after the first dose, and 19, 79, and 142 µg/mL after the fourth dose (16, 77, and 161 µg/mL for single dose in healthy subjects; FIG. 5). The corresponding trough values were 0.66, 2.68, 4.56 µg/mL and 0.98, 3.95 and 7.67 µg/mL for the three dose levels. The mean terminal half-life as calculated after the last dose was approx. 5.5 days.

The safety profile of Peptide 1 was favourable with few adverse events occurring in all treatment groups, including the placebo group, all being mild or moderate. No apparent dose-related trends in incidence or frequency of adverse events were observed. One subject (600 mg group) was withdrawn due to mild infusion reactions.

There were no apparent dose-related trends or treatment related changes in vital signs, ECG, or clinical chemistry parameters (including neutrophil counts, platelet counts, or C-reactive protein levels).

No anti-Peptide 1 antibodies were detected in any of the subjects.

Overall, Peptide 1 was safe and well tolerated when administered i.v. up to 600 mg once weekly for 4 weeks.

Example 4

Modeling of Pharmacokinetic Data

Figure 6:
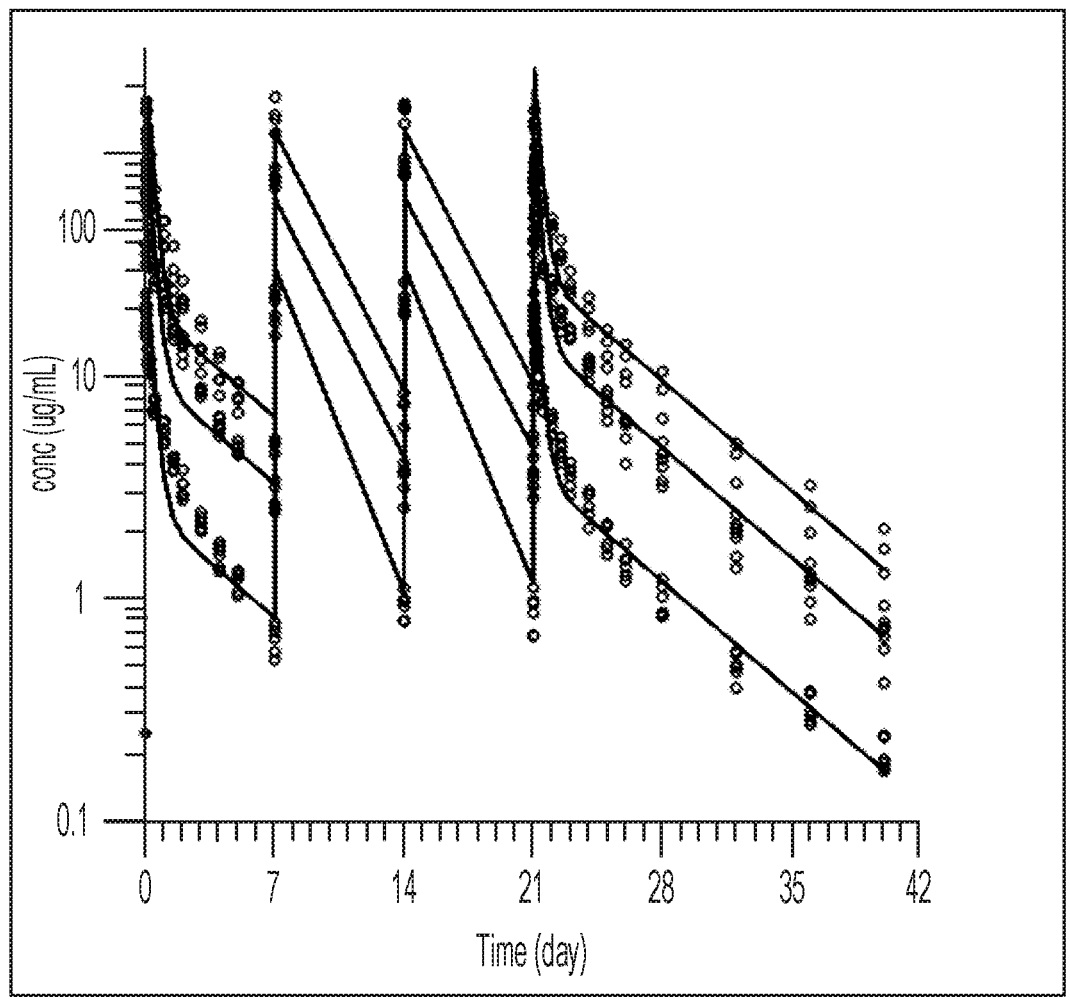
FIG. 6 shows model predictions using a 2-compartment structural PK model (solid line) and observed data (circles) in trial 000115.

The PK data from the 000115 trial can be adequately described using a 2-compartment structural model. Predicted profiles of 75, 300 and 600 mg of Peptide 1 and observed data are depicted in FIG. 6 and the estimated mean PK parameters are listed in Table 1.

TABLE 1

Model Estimates for Peptide 1 Using 2-compartment Structural Pharmacokinetic Model

| Parameter | Estimate | SE | CV % |
|---|---|---|---|
| V | 1.7 L | 0.08 | 4.8 |
| V2 | 8.8 L | 0.32 | 3.6 |
| CL | 3.2 L/day | 0.06 | 1.8 |
| CL2 | 16.4 L/day | 0.24 | 14.4 |

Peptide 1 has a binding affinity in humans of 130 pM to the IL-6/sIL-6R complex. At doses of 75-600 mg, the occupancy level are more than 90% at estimated steady state levels of Peptide 1 using the binding affinity (KD; 130 pM) and the IL-6/sIL-6R levels ($C_{target}$; 2.0 nM based on sIL-6R).

Example 5

Preparation of Peptide 1

Cloning and Expression of Peptide 1 in CHO/dhfr-Cells

CHO/dhfr⁻ cells were obtained from the European collection of cell cultures (ECACC, No. 9406067). The adherent CHO/dhfr⁻ cells are deficient in dihydrofolate reductase (DHFR), an enzyme that catalyses the reduction of folate to dihydrofolate and then to tetrahydrofolate. CHO/dhfr⁻ cells thus display sensitivity to the antifolate drug, methotrexate (MTX).

The CHO/dhfr⁻ cell line is well characterised and tested. The safety of the CHO/dhfr⁻ parental cell line as a cell substrate for the production of biopharmaceuticals for human use was confirmed by ECACC (Porton Down, UK) for microbial sterility, mycoplasma, and adventitious viruses according to 21 CFR.

Selection and Construction of the cDNA Sequence

The cDNA sequence of a monomer of Peptide 1 (the polypeptide sequence of SEQ ID NO: 1) was synthesised as a single DNA fragment by GeneArt AG (Regensburg, Germany) using the sequence for the extracellular domain of gp130 (IL6ST, NCBI Gene ID 3572, transcript variant 1 (NP_002175), amino acids 23-617) and Fc domain of human IgG1 (IGHG1, NCBI Gene ID 3500, amino acids 221-447 according to Kabat EU numbering). The sequence was optimised for optimal codon usage in CHO cells. Three well-characterised point mutations were introduced into the lower hinge region of the Fc part.

The cDNA sequence was further modified by replacing the original gp130 signal peptide with a mouse IgG heavy chain signal peptide of known efficacy in CHO cell expression systems. The signal peptide is cleaved off during protein synthesis. The presence of the IgG1 Cys-Pro-Pro-Cys sequence in the Fc region results in the dimerisation of two identical gp130-Fc subunits via the sulfhydryl residues on the Fc region, which together form Peptide 1.

Figure 7:
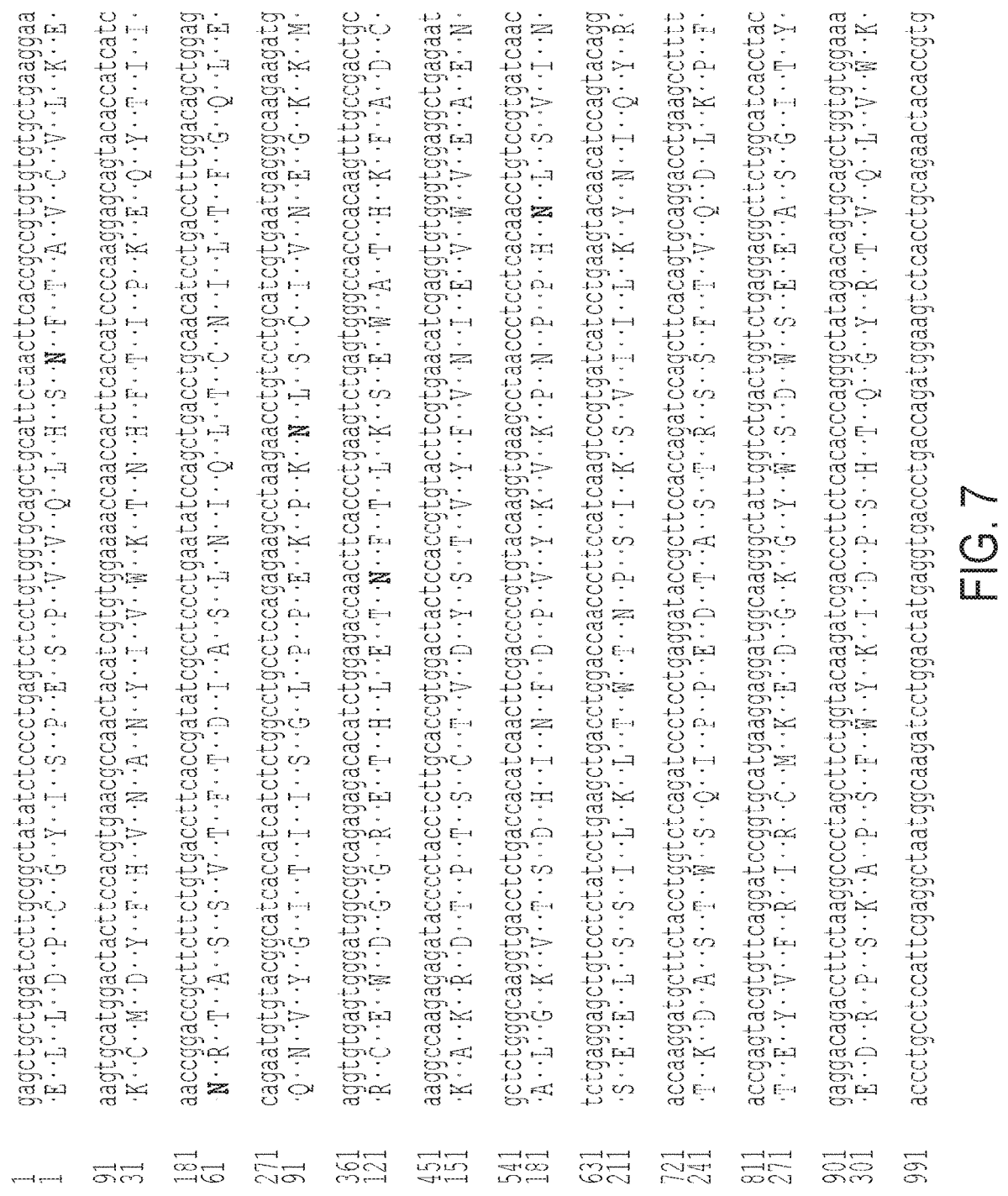
Figure 7:
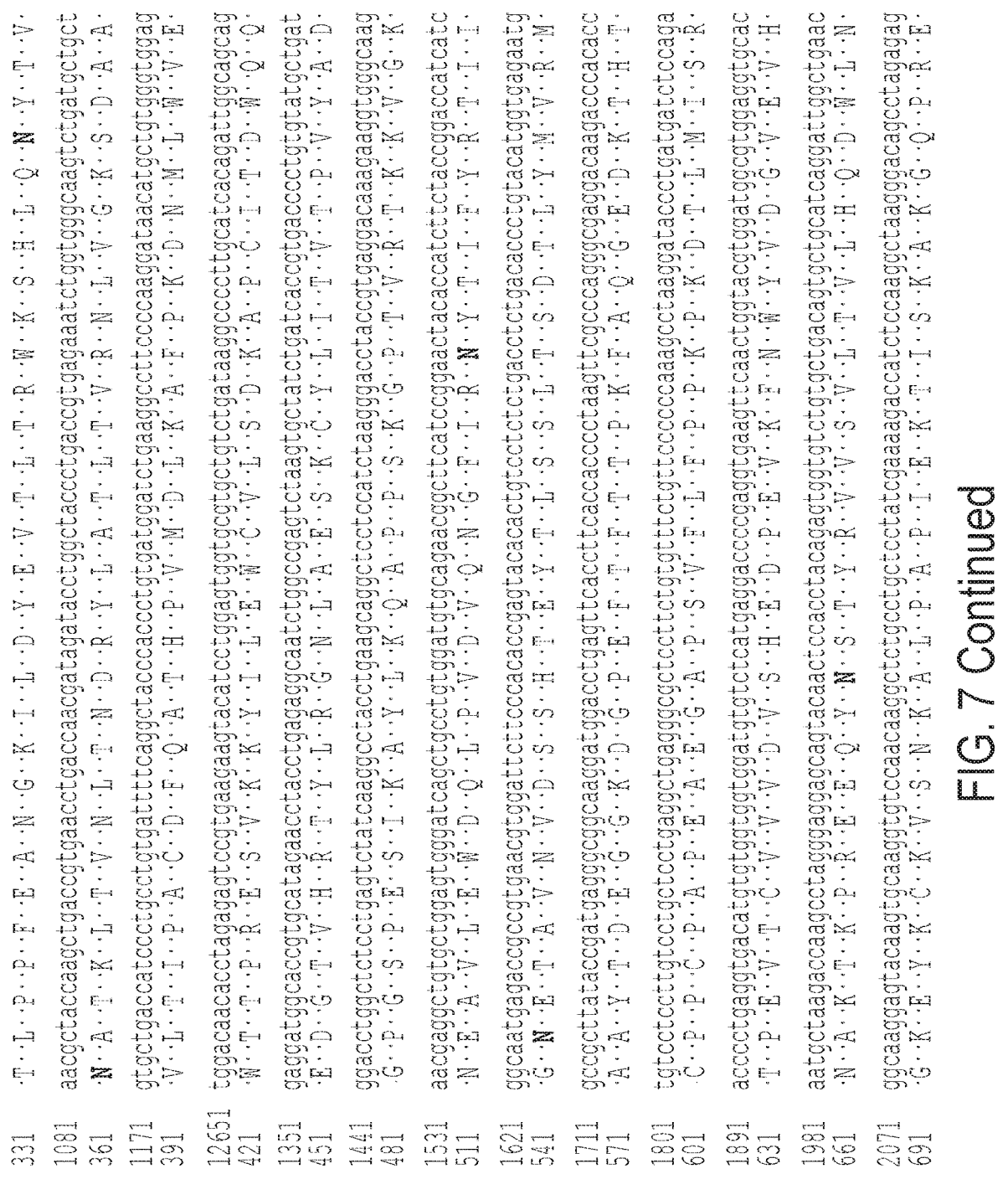

FIG. 7 presents the nucleotide and amino acid sequence of the gp130-Fc subunit used for the formation of Peptide 1.

Construction of the Expression Plasmid for Selection of the Master Cell Bank (MCB)

The monomer cDNA was cloned into a pANTVhG1 expression vector (Antitope) containing the dhfr gene for transfectant selection with MTX as follows: First, the expression vector was digested with MluI and EagI restriction enzymes to permit the insertion of Peptide 1 cDNA. Second, the monomer coding region was PCR amplified using the OL1425 and OL1426 primers (Table 2) and digested with MluI and EagI restriction enzymes. Third, the digested fragments were gel purified and ligated together to generate the pFER02 expression vector. The monomer cDNA was inserted under the control of the cytomegalovirus (CMV) promoter.

Table 3 presents the function of the pFER02 expression elements. FIG. 8 presents the nucleotide sequences of the pFER02 expression elements.

TABLE 2

Oligonucleotide Sequences Used to Amplify the Monomer Coding Region for Cloning into pANTVhG1

| Primer | Sequence (5'-3')* |
|---|---|
| OL1425 | ctgttgct<u>acgcgt</u>gtccactcc GAGCTGCTGGATCCTTGCGGC (SEQ ID NO: 6) |
| OL1426 | gcggggcttg<u>ccggccgt</u>ggcactca CTTGCCAGGAGACAGAGACAG (SEQ ID NO: 7) |

*Monomer 1-specific sequences are shown in upper case, vector-specific sequences are shown in lower case and restriction sites are underlined

TABLE 3 pFER02 Expression Elements

| Feature | Function |
|---|---|
| CMV promoter | Immediate-early promoter/enhancer. Permits efficient, high-level expression of the recombinant protein |
| hIgG1 polyA | Human IgG polyadenylation sequence |
| Ampicillin resistance gene (β-lactamase) | Selection of vector in *E. coli* |
| SV40 early promoter and origin | Allows efficient, high-level expression of the neomycin resistance gene and episomal replication in cells expressing SV40 large T antigen |
| DHFR | Selection of stable transfectants in CHO dhfr-cells |
| SV40 polyadenylation signal | Efficient transcription termination and polyadenylation of mRNA |

Cell Line Selection Process Leading to the Final Peptide 1 Producing Clone

The pFER02 vector was linearised with the blunt-end restriction enzyme SspI, which has a single recognition site located in the beta-lactamase gene. The linearised plasmid was transfected into $5 \times 10^6$ CHO/dhfr⁻ cells using lipid-mediated transfection. Twenty-four hours after transfection, transfected cells were selected in medium supplemented with 5% dialysed foetal calf serum (FCS) and 100 nM methotrexate (MTX). Transfected cells were diluted into this medium at various densities and dispensed into 96-well, flat bottom tissue culture plates. Cells were then incubated in a humidified atmosphere at 5% $CO_2$ and 37° C. Fresh MTX selection medium was added at regular intervals during the incubation time to ensure that MTX levels and nutrient levels remained constant.

Initial Cell Line Selection with MTX selection

For several weeks post transfection, tissue culture plates were examined using a Genetix CloneSelect® Imager, and >2,000 wells were observed to have actively growing colonies. Supernatants from these wells were sampled and assayed for Peptide 1 titre by ELISA. Based on the results of this assay, a total of 105 of the best expressing wells were expanded into 48-well plates. A total of 83 cell lines were selected for expansion into 6-well plates or T-25 flasks; supernatant from each of the cell lines was sampled and assayed for Peptide 1 titre (ELISA). Based on these results, 54 of the best expressing cell lines with optimal growth characteristics were selected for expansion into T-75 or T-175 flasks; supernatants from the confluent flasks were sampled and Peptide 1 titres quantified (ELISA). Comparison of the expression levels between the cell lines allowed for the identification of the 38 best cell lines which were selected for productivity analysis. Productivity was assessed as follows:

Productivity(pg/cell/day)=$((Th-Ti)/((Vh+Vi)/2))$/time

Where:
Th is the harvest titre [μg/mL]
Ti is the initial titre [μg/mL]
Vh is the viable cell count at harvest [$\times 10^6$ cells/mL]
Vi is the initial viable cell count [$\times 10^6$ cells/mL]
Time is the elapsed time (days) between Ti and Th Based on productivity results (pg/cell/day), 13 cell lines were selected for gene amplification.

MTX-Driven Gene Amplification for Peptide 1 Cell Line Selection

The 13 selected cell lines were chosen for the first round of gene amplification by selective pressure under increasing concentrations of MTX (0.1-50 M). After 7-10 days, supernatant from each well from each of the 13 cell lines were sampled and assayed for Peptide 1 titre (ELISA). Wells from each cell line with high Peptide 1 expression levels were assessed for productivity (pg/cell/day). A second round of gene amplification was initiated with a total of 16 wells from cell lines that showed significant increases in productivity.

The second round of gene amplification was conducted in the presence of increased MTX concentrations; supernatants from each culture were assayed for Peptide 1 titre (ELISA). Selected wells from each cell line were expanded and productivity was assessed (pg/cell/day); five cell lines with increased productivity in response to increased MTX selection pressure were identified. These five cell lines were progressed to a third round of gene amplification using selection pressure under increased MTX concentration; supernatants from each well were assayed for Peptide 1 titre (ELISA). Selected wells for each cell line were expanded and productivity (pg/cell/day) was assessed; five cell lines demonstrating high Peptide 1 expression were selected.

Limiting Dilution of Clones

Limiting dilution cloning was performed on the five cell lines demonstrating Peptide 1 expression. After one week of incubation, plates were examined using a Genetix CloneSelect® Imager and single colonies were identified. The growth rates of two cell lines during dilution cloning were noted as being particularly slow and so these cell lines were discontinued. In total, from the three remaining cell lines, 58 clonal colonies were selected for expansion, first into 48-well plates and then successively expanded through 12-well plates, T-25 flasks and T-75 flasks in the absence of MTX. Each of the 58 selected clones was then assessed for productivity (pg/cell/day); 16 clones were selected for suspension adaptation and adaptation to growth in a chemically-defined medium.

Adaptation of Cell Lines to Suspension Culture in Chemically Defined Medium

The 16 cell lines were adapted to suspension culture in a chemically-defined medium as follows: selected cell lines in adherent culture were first adapted to suspension both in CHO suspension growth medium (DMEM high glucose, including L-glutamine and sodium pyruvate, 5% dialysed FCS, 20 mg/L L-proline, 1× penicillin/streptomycin, 1% pluronic F68) and then in chemically defined suspension growth medium (CD Opti-CHO® from Life Technologies Ltd. (Paisley, UK), 2.5% dialysed FCS, 0.1× penicillin/streptomycin, 8 mM Glutamax®).

Once adapted to suspension culture, the cell lines were weaned, in stages, into a serum-free chemically-defined suspension growth medium (CD Opti-CHO®, 0.1× penicillin/streptomycin, 8 mM Glutamax®). MTX was omitted from all suspension cultures. The adapted lines were expanded and seed cell banks were prepared. Briefly, cells were expanded to 300 mL total volume and harvested when cell density exceeded $0.85 \times 10^6$ cells/mL and viability was >90%. A further $3 \times 10^7$ cells were seeded into a fresh flask containing 70 mL suspension growth medium for growth and productivity analysis. The remaining cells were harvested by centrifugation and resuspended in an appropriate volume of freezing medium to yield a cell suspension at $1 \times 10^7$ cells/mL. Vials were frozen down to −80° C. The cell bank was then transferred to liquid nitrogen for long-term storage.

The 16 cell lines were further refined down to 5 clones after serum-free adaptation. The 5 clones were assessed for growth (cell density and cell doubling time) and productivity (pg/cell/day), after which 3 clones were selected. One clone was selected to make a master cell bank.

Preparation of the master cell bank (MCB) and working cell bank (WCB) was carried out. One vial from the pre-seed stock was used for the preparation of a 200 vial MCB, and one vial of MCB was used to prepare a 200 vial WCB. In each case, a vial was thawed and the cryopreservation medium removed by centrifugation. The cells were resuspended and propagated in volume in growth medium (CD OptiCHO®/4 mM L-glutamine). Four passages were performed during the creation of MCB and six passages were performed during the creation of WCB.

When sufficient cells were obtained, cells were aliquoted in cryopreservation medium (92.5% CD OptiCHO®/7.5% DMSO) into polypropylene vials (each containing approximately $1.5 \times 10^7$ viable cells) and cryopreserved by reducing the temperature to −100° C. over a period of at least 60 minutes in a gradual freezing process. Vials are stored in a vapour phase liquid nitrogen autofill container in a GMP controlled area.

Description of the Drug Substance (DS) Manufacturing Process

A brief description of the Peptide 1 DS manufacturing process is as follows. Cells from a WCB vial are revived and progressively expanded using protein-free medium prior to inoculation into a production bioreactor. Upon completion of the cell culture, cells and cell debris are removed by filtration of the culture.

Purification consists of three chromatography column steps (MAbSelect Sure, SP Sepharose, Capto Q or Sartobind Phenyl), a concentration and diafiltration step and includes two specific viral reduction/inactivation steps; Triton X-100 (inactivation of enveloped viruses) treatment and a nanofiltration step (removal of enveloped and non-enveloped viruses).

Following concentration and diafiltration, excipients are added for the formulation of the DS. The formulated Peptide 1 is 0.22 μm filtered into containers.

Description and Composition of the Drug Product (DP)

The DP is a sterile solution to be administered by i.v. infusion. The DP consists of Peptide 1 at a concentration of 15 mg/mL in an isotonic solution containing 25 mM L-histidine, 200 mM sucrose and 0.1 mg polysorbate 20/mL at pH 7.6. The vials are overlaid with nitrogen for protection against oxidation. The product is intended for single use and storage at −20° C. until thawing for clinical administration.

Composition and Batch Formula

The batch formula for the drug product is presented in Table 4.

TABLE 4

DP Batch Composition

| Component | Amount | Quality standard |
| --- | --- | --- |
| Peptide 1 | 720 g | Ferring specification |
| L-Histidine | 186.18 g | Ph. Eur./USP* |
| Sucrose | 3286.08 g | Ph. Eur./USP* |
| Polysorbate 20 | 4.8 g | Ph. Eur./USP* |
| WFI | ad 49536 g | Ph. Eur./USP* |
| Sodium hydroxide | quantum satis | Ph. Eur./USP* |
| Nitrogen | quantum satis | Ph. Eur./USP* |

*curr. Ed.

The invention claimed is:

1. A method for the treatment of an inflammatory disease or an IL-6- mediated condition in a human, said method comprising administering to a human in need thereof an effective amount of a polypeptide dimer that inhibits IL-6 trans-signaling, wherein the polypeptide dimer comprises two monomers, each monomer comprises an amino acid sequence having at least 95% sequence identity to SEQ ID NO: 1, and comprises the gp130 D6 domain corresponding to the amino acids at positions 585-595 of SEQ ID NO: 1, and an Fc domain hinge region comprising the amino acids at positions 609-612 of SEQ ID NO: 1, and each monomer does not comprise a linker between the gp130 D6 domain and the Fc domain hinge region; wherein the effective amount is 60 mg to 750 mg of the polypeptide dimer; and wherein the polypeptide dimer is administered every 7-60 days.

2. The method of claim 1, wherein each monomer comprises the amino acid sequence of SEQ ID NO: 1.

3. The method of claim 1, wherein the effective amount is 60 mg to 600 mg.

4. The method of claim 1, wherein the polypeptide dimer is administered every 7-30 days.

5. The method of claim 4, wherein the polypeptide dimer is administered every 7-20 days.

6. The method of claim 1, wherein the polypeptide dimer is administered every 7-14 days.

7. The method of claim 1, wherein the polypeptide dimer is administered every 7 days.

8. The method of claim 1, wherein the polypeptide dimer is administered every 14 days.

9. The method of claim 1, wherein the polypeptide dimer is administered parenterally.

10. The method of claim 1, wherein the polypeptide dimer is administered intravenously or subcutaneously.

11. The method of claim 1, wherein the inflammatory disease or IL-6-mediated condition is inflammatory bowel disease.

12. The method of claim 11, wherein the inflammatory bowel disease is Crohn's disease or ulcerative colitis.

13. The method of claim 11, wherein the treatment induces or maintains the remission of inflammatory bowel disease.

14. The method of claim 1, wherein the inflammatory disease or IL-6-mediated condition is rheumatoid arthritis, psoriasis, uveitis or atherosclerosis.

15. The method of claim 1, wherein neutrophil counts, platelet counts and/or levels of C-reactive protein are maintained within a physiologically normal range after administration of the polypeptide dimer.

16. The method of claim 1, wherein the treatment further comprises the administration of a second active agent.

17. The method of claim 16, wherein the second active agent is 5-aminosalicylic acid, azathioprine, 5-mercaptopurine or a corticosteroid.

* * * * *